(12) United States Patent
Lynch et al.

(10) Patent No.: US 11,922,626 B2
(45) Date of Patent: *Mar. 5, 2024

(54) SYSTEMS AND METHODS FOR AUTOMATIC DETECTION AND QUANTIFICATION OF PATHOLOGY USING DYNAMIC FEATURE CLASSIFICATION

(71) Applicant: National Jewish Health, Denver, CO (US)

(72) Inventors: David A. Lynch, Denver, CO (US); Stephen M. Humphries, Denver, CO (US)

(73) Assignee: National Jewish Health, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/950,376

(22) Filed: Sep. 22, 2022

(65) Prior Publication Data
US 2023/0260108 A1    Aug. 17, 2023

Related U.S. Application Data

(63) Continuation of application No. 17/330,088, filed on May 25, 2021, now Pat. No. 11,468,564, which is a
(Continued)

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0062* (2013.01); *A61B 5/055* (2013.01);
(Continued)

(58) Field of Classification Search
CPC ..... G06T 7/0012; A61B 5/0062; A61B 5/055; A61B 6/5217; A61B 6/03; G06N 5/022;
(Continued)

(56) References Cited

U.S. PATENT DOCUMENTS

| | | | |
|---|---|---|---|
| 5,463,548 A | 10/1995 | Asada et al. | |
| 6,466,687 B1 * | 10/2002 | Uppaluri | ............... G06T 7/0012 |
| | | | 382/128 |

(Continued)

OTHER PUBLICATIONS

Anthimopoulos et al. "Lung Pattern Classification for Interstitial Lung Diseases Using a Deep Convolutional Neural Network," IEEE Transactions on Medical Imaging, May 2016, vol. 35, No. 5, pp. 1207-1216.

(Continued)

*Primary Examiner* — Tom Y Lu
(74) *Attorney, Agent, or Firm* — Sheridan Ross P.C.

(57) ABSTRACT

Methods, devices, and systems are provided for quantifying an extent of various pathology patterns in scanned subject images. The detection and quantification of pathology is performed automatically and unsupervised via a trained system. The methods, devices, and systems described herein generate unique dictionaries of elements based on actual image data scans to automatically identify pathology of new image data scans of subjects. The automatic detection and quantification system can detect a number of pathologies including a usual interstitial pneumonia pattern on computed tomography images, which is subject to high inter-observer variation, in the diagnosis of idiopathic pulmonary fibrosis.

20 Claims, 13 Drawing Sheets

Related U.S. Application Data continuation of application No. 16/886,551, filed on May 28, 2020, now Pat. No. 11,494,902, which is a continuation of application No. 15/595,260, filed on May 15, 2017, now Pat. No. 10,706,533.

(60) Provisional application No. 62/335,816, filed on May 13, 2016.

(51) Int. Cl.

| | |
|---|---|
| A61B 5/055 | (2006.01) |
| A61B 6/00 | (2006.01) |
| G06N 5/022 | (2023.01) |
| G06N 20/10 | (2019.01) |
| G16B 40/20 | (2019.01) |
| G16B 40/30 | (2019.01) |
| G16B 50/30 | (2019.01) |
| G16B 99/00 | (2019.01) |
| G16H 30/40 | (2018.01) |
| G16H 50/20 | (2018.01) |
| A61B 6/03 | (2006.01) |

(52) U.S. Cl.
CPC ........... *A61B 6/5217* (2013.01); *G06N 5/022* (2013.01); *G06N 20/10* (2019.01); *G16B 40/20* (2019.02); *G16B 40/30* (2019.02); *G16B 50/30* (2019.02); *G16B 99/00* (2019.02); *G16H 30/40* (2018.01); *G16H 50/20* (2018.01); *A61B 6/03* (2013.01)

(58) Field of Classification Search
CPC ........ G06N 20/10; G16B 40/20; G16B 40/30; G16B 50/30; G16B 99/00; G16H 30/40; G16H 50/20

See application file for complete search history.

(56) References Cited

U.S. PATENT DOCUMENTS

| | | | |
|---|---|---|---|
| 9,582,880 | B2 | 2/2017 | Kim et al. |
| 10,074,038 | B2 | 9/2018 | Hseih et al. |
| 10,706,533 | B2 * | 7/2020 | Lynch .................... G06N 20/10 |
| 10,910,094 | B2 | 2/2021 | Hartung et al. |
| 11,468,564 | B2 | 10/2022 | Lynch et al. |
| 11,494,902 | B2 | 11/2022 | Lynch et al. |
| 2003/0103665 | A1 | 6/2003 | Uppaluri et al. |
| 2006/0018524 | A1 | 1/2006 | Suzuki et al. |
| 2008/0292194 | A1 | 11/2008 | Schmidt et al. |
| 2013/0004044 | A1 | 1/2013 | Ross et al. |
| 2015/0254842 | A1 | 9/2015 | Brown |
| 2018/0300878 | A1 | 10/2018 | Ihara |
| 2018/0322660 | A1 | 11/2018 | Smith |
| 2018/0365829 | A1 | 12/2018 | Madabhushi et al. |
| 2019/0026897 | A1 | 1/2019 | Wu et al. |
| 2019/0138888 | A1 | 5/2019 | Sekiyama et al. |

OTHER PUBLICATIONS

Best et al. Quantitative CT Indexes in Idiopathic Pulmonary Fibrosis: Relationship with Physiologic Impairment, Radiology, Aug. 2003, vol. 228, No. 2, pp. 407-414.
Halevy et al. "The Unreasonable Effectiveness of Data," IEEE Intelligent Systems, Mar./Apr. 2009, vol. 24, No. 2, pp. 8-12.
Hansell et al. "CT staging and monitoring of fibrotic interstitial lung diseases in clinical practice and treatment trials: a Position Paper from the Fleischner Society," The Lancet Respiratory Medicine, vol. 3, No. 6, pp. 483-496 (Abstract Only).
Humphries et al. "Idiopathic Pulmonary Fibrosis: Data-driven Textural Analysis of Extent of Fibrosis at Baseline and 15-Month Follow-up," Radiology, Oct. 2017, vol. 285, No. 1, pp. 270-278.
Hunninghake et al. "MUC5B Promoter Polymorphism and Interstitial Lung Abnormalities," The New England Journal of Medicine, Jun. 2013, vol. 368, No. 23, pp. 2192-2200.
Iwasawa et al. "Assessment of Prognosis of Patients With Idiopathic Pulmonary Fibrosis by Computer-aided Analysis of CT Images," J Thorac Imaging, Aug. 2009, vol. 24, No. 3, pp. 216-222.
Jacob et al. "Automated Quantitative Computed Tomography Versus Visual Computed Tomography Scoring in Idiopathic Pulmonary Fibrosis: Validation Against pulmonary Function," J Thorac Imaging, Sep. 2016, vol. 31, No. 5, pp. 304-311.
Kalinovsky et al. "Lung Image Segmentation Using Deep Learning Methods and Convolutional Neural Networks," XIII International Conference on Pattern Recognition and Information Processing, 2016, pp. 21-24.
Kim et al. "Classification of parenchymal abnormality in scleroderma lung using a novel approach to denoise images collected via a multicenter study," Acad Radiol., Aug. 2008, vol. 15, No. 8, pp. 1004-1016.
Kim et al. "Comparison of the Quantitative CT Imaging Biomarkers of Idiopathic Pulmonary Fibrosis at Baseline and Early Change with an Interval of 7 Months," Academic Radiology, Jan. 2015, vol. 22, No. 1, pp. 70-80.
Landis et al. "The Measurement of Observer Agreement for Categorical Data," Biometrics, Mar. 1977, vol. 33, No. 1, pp. 159-174.
Ley et al. "Idiopathic Pulmonary Fibrosis: CT and Risk of Death," Radiology, Nov. 2014, vol. 273, No. 2, pp. 570-579.
Lynch et al. "High-Resolution Computed Tomography in Idiopathic Pulmonary Fibrosis," Am J Respir Crit Care Med, 2005, vol. 172, pp. 488-493.
Park et al. "Texture-Based Automated Quantitative Assessment of Regional Patterns on Initial CT in Patients With Idiopathic Pulmonary Fibrosis: Relationship to Decline in Forced Vital Capacity," AJR Am J Roentgenol, Nov. 2016, vol. 207, No. 5, pp. 976-983.
Pathak et al. "Constrained Convolutional Neural Networks for Weakly Supervised Segmentation," ICCV 2015, 12 pages [arXiv:1506.03648v2].
Raghu et al. "An official ATS/ERS/JRS/ALAT statement: idiopathic pulmonary fibrosis: evidence-based guidelines for diagnosis and management," American Journal of Respiratory and Critical Care Medicine, Mar. 2011, vol. 183, No. 6, pp. 788-824.
Shelhamer et al. "Fully Convolutional Networks for Semantic Segmentation," IEEE Conference on Computer Vision and Pattern Recognition (CVPR), May 2015, 12 pages [arXiv:1605.06211v1].
Shin et al. "Deep Convolutional Neural Networks for Computer-Aided Detection: CNN Architectures, Dataset Characteristics and Transfer Learning," IEEE Transactions on Medical Imaging, 2016, vol. 35, No. 5, pp. 1285-1298.
Wang et al. "A two-step Convolutional Neural Network based Computer-aided detection scheme for automatically segmenting adipose tissue volume depicting on CT images," Compute Methods Programs Biomed., Jun. 2017, vol. 144, pp. 97-104.
Watadani et al. "Interobserver Variability in the CT Assessment of Honeycombing in the Lungs," Radiology, Mar. 2013, vol. 266, No. 3, pp. 936-944.
Wells "The revised ATS/ERS/JRS/ALAT diagnostic criteria for idiopathic pulmonary fibrosis (IPF)—practical implications," Respiratory Research, Apr. 2013, vol. 14, Supplement 1, article 52, 6 pages.
Yang et al. "Automatic Liver Segmentation Using an Adversarial Image-to-Image Network," Medical Image Computing and Computer-Assisted Intervention—MICCAI 2017, Jul. 2017, 8 pages [arXiv:1707.08037v1].
Zach et al. "Quantitative CT of the Lungs and Airways in Healthy Nonsmoking Adults," Invest Radiol., Oct. 2012, vol. 47, No. 10, pp. 596-602.

* cited by examiner

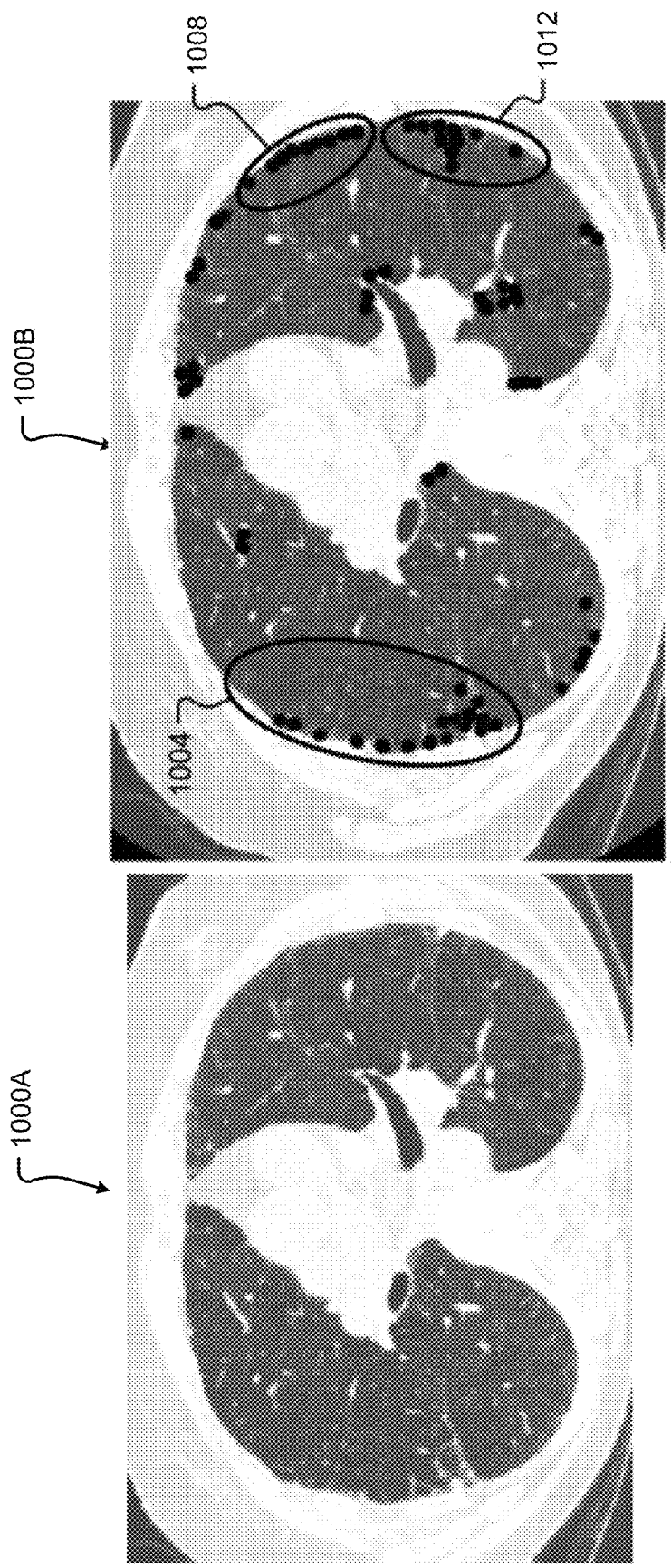

SYSTEMS AND METHODS FOR AUTOMATIC DETECTION AND QUANTIFICATION OF PATHOLOGY USING DYNAMIC FEATURE CLASSIFICATION

CROSS-REFERENCE TO RELATED APPLICATIONS

This application is a continuation of U.S. application Ser. No. 17/330,088, filed May 25, 2021, now U.S. Pat. No. 11,468,564, which is a continuation of U.S. application Ser. No. 16/886,551, filed May 28, 2020, which is a continuation of U.S. application Ser. No. 15/595,260, filed May 15, 2017, now U.S. Pat. No. 10,706,533, which claims the benefit of priority under 35 U.S.C. § 119(e) to U.S. Provisional Patent Application No. 62/335,816, filed May 13, 2016. The entire disclosure of U.S. Provisional Patent Application No. 62/335,816 is incorporated herein by reference.

FIELD

The present disclosure is generally directed to computer diagnostic systems and more specifically to systems for automatically detecting and quantifying pathology in scanned images.

BACKGROUND

In general, certain pathologies manifest as abnormalities in the tissues of a subject or patient. While these abnormalities may not be detectable during a routine exam, symptoms of the pathology may cause a diagnosing professional to recommend and/or administer various imaging scans of a subject to obtain images of suspect tissues/areas. Existing systems for reviewing imaging scans rely on human interaction and are prone to misclassification and misidentification of pathologies. While diagnosing and treating irregularities in patients is often time-critical and urgent, the time required to confidently identify and/or classify the presence, location and/or extent of such irregularities and normal tissues through contemporary methods is typically great, often at the risk of a patient's health.

Besides consuming time at a time-critical moment, contemporary methods of identifying and/or classifying the presence, location and/or extent of such irregularities and normal tissues require great expertise. Typically today's imagers are required to be licensed and board certified and complete medical school training and years of postgraduate training in the form of a residency. Even still, misidentification and/or misclassification occurs often and second or third opinions may be required. As a result, experts capable of reviewing imaging scans for irregularities are rarely readily accessible, causing more of a time delay, are not always correct, and may increase medical expenses.

Also, while such imaging scans are used around the world to classify and identify irregularities, interaction and collaboration between doctors is either rare or impossible in many circumstances. In fact, some pathologies maybe undetectable by the human eye. For example, while a doctor in one country may have a special ability to identify a particular irregularity, another doctor in another country may lack such an ability and cannot access such information. As a result, today's methods of reviewing imaging scans and identifying and/or classifying irregularities has resulted in a wealth of information that cannot easily be shared.

Furthermore, many patients around the world have limited access to healthcare and particularly lack access to such experts as would be able to identify rare diseases by reviewing medical scans through contemporary methods. As the cost of machines capable of generating imaging scans decreases through advancing technology, the world population is increasing and thus the ratio of patients to doctors throughout the world is growing at an increasing rate. Thus methods and systems of identifying such irregularities without the requirement of a trained medical expert is greatly needed.

Finally, in some cases, a diagnosing professional may review whether a pathology has changed over time. In any event, this assessment of change is susceptible to interpretation error, inter-observer variation, variations in scan quality, and is generally subjective in nature. As such, proper patient care using contemporary techniques may require routine reviews of medical scans. Accordingly, today's imaging experts may be incapable of personally reviewing each and every scan of every potential irregularity throughout the world in the short time that a patient may need such a review.

SUMMARY

It is with respect to the above issues and other problems that the embodiments presented herein were contemplated. What is needed is a time-efficient, accurate, fast-learning, method of identifying and/or classifying irregularities in imaging scans which does not require an expert in pathology and is capable of detecting irregularities which may not be detectable by even an expertly trained human eye. In general, embodiments of the present disclosure provide methods, devices, and systems for quantifying an extent of various pathology patterns in scanned subject images. Scanned images may include images received from any imaging modality. For instance, imaging modalities may include, but are in no way limited to, computed tomography (CT), magnetic resonance imaging (MM), optical microscopy, or other biomedical imaging modality capable of producing image data. In one embodiment, the diagnosis and quantification of pathology may be performed automatically and unsupervised via a computer system. For instance, the methods, devices, and systems described herein may be used to automatically identify a usual interstitial pneumonia (UIP) pattern on computed tomography (CT) images of the lungs, which is subject to high inter-observer variation, in the diagnosis of idiopathic pulmonary fibrosis (IPF).

While described in conjunction with identifying and quantifying extent of UIP, or lung fibrosis, on CT images, it should be appreciated that the various embodiments described herein are not so limited. For example, the methods, devices, and systems disclosed herein may be used to identify and/or quantify any pathology capable of producing distinguishing patterns in local regions of scanned image data (e.g., where scanned image data is different, or distinguishable, between healthy tissue and pathological tissue, etc.). Moreover, embodiments of the present disclosure are not limited to the lungs of a subject and may apply to any region, area, site, or portion of a subject capable of producing distinguishing scanned image data.

In some embodiments, the quantification of imaging abnormalities includes employing a set of features or basis elements, or a dictionary of elements, representing features of relatively small image regions and/or features of image regions at multiple scales depicting normal tissue and/or pathology. Once generated, the dictionary may be used to encode other image regions. In some embodiments, the dictionary can be generated by receiving image data scans of a particular area with and/or without pathology taken from a number of subjects. Local regions, or blocks, may be extracted from these image data and an initial analysis such as clustering applied to determine, or "learn," a number of feature representations. The sizes, configurations and dimensionality of blocks may vary depending on application. In one embodiment, the resulting dictionary may include elements that represent low-level features such as directed edges or blobs. In any event, other novel image regions, not included in the dictionary construction process, may be reconstructed mathematically using weighted combinations of dictionary elements. Various methods may be used to determine weighting coefficients, which provide descriptive quantitative features useful in subsequent classification analysis. Pooling weighting coefficients over image regions of a larger scale than dictionary elements, for example by averaging weighting coefficients computed within a region several times the size of dictionary elements, produces distinctive quantitative signatures.

Technical improvements provided by the disclosure may relate to the complexity of the "dictionary elements" and how they are computed. In certain embodiments, hierarchical features, i.e. more complicated dictionary elements may be used where higher level elements are computed in terms of lower level dictionary elements. These hierarchical features may take into account more image context (not just one small sliding window) by concatenating multiple layers of dictionary features at different image scales.

In some embodiments, clustering operations (e.g. k-means) may be used to develop the feature dictionary. In some embodiments, mathematical optimization may be used to develop and/or fine tune or refine dictionary elements to maximize classification accuracy, e.g. update a previously computed dictionary so the best elements for a given classification task are included. In this context the dictionary elements could be referred to as "convolutional filters".

In some embodiments, a classification model utilizing features contained in a dictionary may be trained in a supervised fashion using expert labeled examples. In some embodiments, the process may comprise classifying image regions into one of a number of categories defined by expert labeled exemplars. In a lung classification application this may produce a composite score for a subject. For example, 80% of sampled image regions classified as normal lung, 12% classified as reticular abnormality, 5% classified as honeycombing and 3% not classified. In some embodiments, a classification model may be trained in an unsupervised fashion not reliant on expert labeled image regions for training. In some embodiments, an additional clustering process may be used to classify tissue types instead of supervised training using expert labeled images. With this additional clustering classification categories may not have semantic labels or expert assigned names such as normal, reticular abnormality or honeycombing, in which case a composite classification score may be 3% category 1, 0.8% category 2, . . . 1% category N wherein the sum over all N categories is 100%.

By way of example, a number of image data scans (e.g., generated by computed tomography, etc.) may be taken of the lungs of subjects with and without pathology (e.g., having IPF and not having IPF, etc.). The image data scans may include multiple scans taken from each subject. Utilizing a fixed block size (e.g., 3 mm×3 mm, etc.), a computer system may automatically extract image blocks from within a defined area of the image data scan. This analysis may include moving along a path within the defined area and extracting image blocks of fixed size that are adjacent to one another. Additionally or alternatively, the analysis may include extracting blocks of varying size from one or more image blocks that are overlapping one another within the defined area. It should be appreciated, that the block size may correspond to a defined pixel area. In any event, a clustering process (e.g., a modified k-means clustering process, etc.) or optimization process may be applied to the pixel intensities in each of the extracted blocks to produce a dictionary of elements (e.g., an element dictionary of image data scan patterns found in the lungs, etc.). Various mathematical pre-processing methods (e.g. data whitening and/or contrast normalization) may be applied prior to clustering depending on the application. As pixel intensities or luminance may vary across a length and/or a width of an extracted block, each element in the dictionary may be generated to uniquely describe or characterize a scanned feature or a portion thereof defined by the variation in pixel intensity and/or luminance over distance. In some embodiments, pixel intensities may be preferred over luminance values. For example, in CT images, the brightness of pixels is proportional to material density and CT pixel values are usually expressed on an established scale (called the Hounsfield Unit (HU) scale). Larger image regions (e.g. 14×14 mm) can be described by pooling (e.g. by average or maximum values) dictionary element weighting coefficient values for each overlapping block within the region.

Once the dictionary is generated, an automatic detection and quantification system may be constructed to classify image regions demonstrating normal and abnormal tissue in other subjects. The classification system may be based on supervised training where an expert (e.g., experienced radiologist, etc.) delineates and labels regions of interest (ROIs) in representative image data scans that demonstrate the characteristic patterns of a specific pathology (e.g., UIP, etc.). In the example above, characteristics of UIP include patterns generally known as honeycombing, reticular abnormality, and traction bronchiectasis. This delineation may be performed by outlining or otherwise identifying regions in the image data scans. In some embodiments, the delineated regions may be verified by another expert (e.g., another experienced radiologist, a senior thoracic radiologist, etc.) before using the delineations in training the automatic detection and quantification system. Utilizing the previously constructed dictionary, quantitative features may be computed for each of the ROIs.

Next, the ROIs and associated quantitative features, or labeled exemplars, are presented to a classifier algorithm for training. A variety of classifier algorithms including artificial neural network (ANN), Support Vector Machine (SVM), Logistic Regression (LR) or Random Forest (RF) may be used separately or as an ensemble. In some embodiments, the labeled exemplars may be used to form training examples for the classifier algorithm. In one embodiment, each of the training examples is marked as being associated with a particular characteristic pattern of a specific pathology, or classification category. In response to receiving the training examples, the classifier algorithm may generate a predictive model that is configured to classify new image scan data as being associated with one or more of the characteristic patterns of specific pathology, or categories. In some embodiments, the classifier algorithm may be trained to identify whether regions of a new image data scan are associated with normal or pathological tissue (e.g., normal or fibrotic lung, etc.). These regions may be automatically classified and/or marked by the classifier algorithm for each scan. In one embodiment, only tissue having pathology is marked or otherwise identified by the classifier algorithm. In any event, the classifier algorithm may analyze a new image data scan and automatically determine areas of tissue having pathology according to any classification category. A total quantitative score may be generated, for example by computing fraction of regions classified as abnormal.

As can be appreciated, the automatic detection and quantification system described herein may quickly and accurately determine a particular characteristic pattern of a specific pathology in a subject using quantifiable data evaluation techniques. Unlike human interpretation, or qualitative analysis, the methods, devices, and systems as described herein are in no way affected by user error, user bias, or inter-observer variation. In addition, the automatic detection and quantification system is capable of performing an analysis on tens, hundreds, or even thousands of image data scans in fractions of a second. At least one benefit to the system described herein is that each image data scan associated with subject, which may amount to hundreds or even thousands of scans per subject, can be quickly and accurately checked to ensure that any existent or detectable pathology is found. As disclosed herein, the system may be used on two-dimensional (2D) image sections, three-dimensional (3D) image volumes, and/or other multi-dimensional image representations.

The term "computer-readable medium," as used herein, refers to any tangible data storage medium that participates in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, or any other medium from which a computer can read instructions. When the computer-readable medium is configured as part of a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The terms "determine," "calculate," and "compute," and variations thereof, as used herein, are used interchangeably and include any type of methodology, process, mathematical operation, or technique.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "module" as used herein refers to any known or later developed hardware, software, firmware, artificial intelligence, fuzzy logic, or combination of hardware and software that is capable of performing the functionality associated with that element.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 10A shows a sample image data scan of a subject in accordance with embodiments of the present disclosure;

FIG. 10B shows the image data scan of FIG. 10A including regions of interest identified by the automatic detection and quantification system in accordance with embodiments of the present disclosure;

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
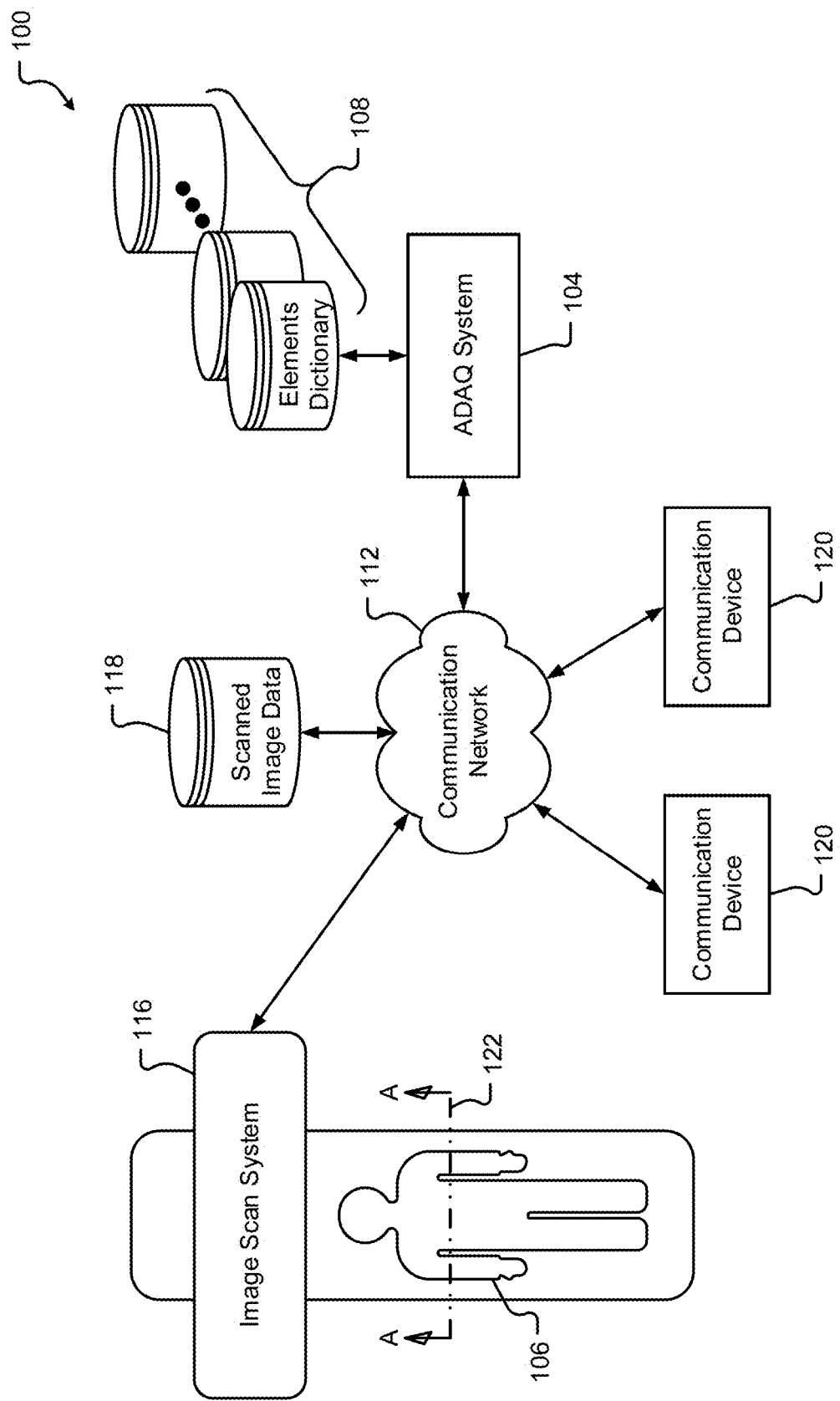
FIG. 1 is a diagram depicting an automatic detection and quantification system in a communications environment in accordance with embodiments of the present disclosure.

FIG. 1 is a diagram depicting an automatic detection and quantification system in a communications environment 100 in accordance with embodiments of the present disclosure. The environment 100 includes an automatic detection and quantification (ADAQ) system 104 with one or more elements dictionaries 108. In one embodiment, the ADAQ system 104 may be referred to as a data-driven textural analysis (DTA) system. In any event, the ADAQ system 104 may be configured to receive scanned image data across a communication network 112. This scanned image data may be stored in a memory 118 after an image scan system 116 scans a subject 106. In some embodiments, the ADAQ system 104 may communicate with one or more communication devices 120 across the communication network 112. This communication may include, but is in no way limited to, transferring files, exchanging information, providing results in a digital format, causing the communication device 120 to render the results of an analysis performed by the ADAQ system 104 of a subject, etc.

The elements dictionary 108 may be stored in a memory communicatively coupled with the ADAQ system 104. In some embodiments, the elements dictionary may be stored in a memory across the communication network 112 (e.g., in the cloud, etc.). This storage can allow for an elements dictionary 108 developed for a particular pathology, or type of pathology, to be uploaded and/or stored remotely from a particular ADAQ system 104. Continuing this example, the elements dictionary 108 may be accessed and used by other ADAQ systems 104 in quantifying pathology in other subjects. For instance, an elements dictionary 108 may be developed by an ADAQ system 104 in a particular geographical location and uploaded, or stored, in a cloud memory. This elements dictionary 108 may subsequently be used, accessed, or downloaded by another ADAQ system 104 in different geographical location. Among other things, this approach allows multiple ADAQ systems, worldwide, to access the information (e.g., the elements dictionary, etc.) stored in the cloud. As can be appreciated, a diagnostic professional is provided instant or near-instant access to the various stored elements dictionaries 108 for specific pathologies. Using an ADAQ system 104 and the relevant elements dictionary 108, the diagnostic professional may detect and quantify pathology of subjects anywhere the world.

In some embodiments, the elements dictionary 108 may be updated. The update may include refining elements, providing additional description for element patterns, adding elements, and/or otherwise modifying the data stored in the elements dictionary 108.

The communication network 112 may comprise any type of known communication medium or collection of communication media and may use any type of protocols to transport messages between endpoints. The communication network 112 may include wired and/or wireless communication technologies. The Internet is an example of the communication network 112 that constitutes an Internet Protocol (IP) network consisting of many computers, computing networks, and other communication devices located all over the world, which are connected through many telephone systems and other means. Other examples of the communication network 112 include, without limitation, a standard Plain Old Telephone System (POTS), an Integrated Services Digital Network (ISDN), the Public Switched Telephone Network (PSTN), a Local Area Network (LAN), a Wide Area Network (WAN), a Voice over Internet Protocol (VoIP) network, a cellular network, and any other type of packet-switched or circuit-switched network known in the art. In addition, it can be appreciated that the communication network 112 need not be limited to any one network type, and instead may be comprised of a number of different networks and/or network types. The communication network 112 may comprise a number of different communication media such as coaxial cable, copper cable/wire, fiber-optic cable, antennas for transmitting/receiving wireless messages, and combinations thereof.

The image scan system 116 may include any device, machine, or system that is configured to scan an area or volume of a subject and generate image data representative of that area or volume. An image scan system 116 may be configured to generate image data of areas inside a subject (e.g., areas that cannot be observed, monitored, or detected from outside of the subject, etc.). In some embodiments, the image scan system 116 may be a computed tomography (CT) system. For instance, the CT system may generate images of areas or regions inside a subject's body using x-rays taken in stepped increments or sections. Scan sections may be taken along one or more cross-sections 122 of a subject body as illustrated by cross-section A-A. The scans may be made at fixed increments (e.g., 0.5 mm, 1.0 mm, 2.0 mm, and so on). When the scans are combined, a three-dimensional image may be generated of the inside of a subject volume, or portions thereof. Although discussed in conjunction with CT scanners and the like, it should be appreciated that the ADAQ system may receive image data scans from any imaging or image scan system in generating element dictionaries and/or quantifying pathology in subject images. For instance, image data scans may be generated by magnetic resonance imaging (Mill) machines, X-ray machines, ultrasound machines, optical imaging modalities (e.g. microscope, etc) etc. While described as using 2D imaging data, it should be appreciated that embodiments of the present disclosure may similarly use 3D image data. In this case, the various regions/patches/blocks etc. may be an image volume (e.g., 28×28×28 voxels) or three 2D orthogonal image planes (e.g., each 28×28 pixels) that intersect at a point of interest.

The scanned image data memory 118 may be one or more disk drives, optical storage devices, solid-state storage devices such as a random access memory ("RAM") and/or a read-only memory ("ROM"), which can be programmable, flash-updateable and/or the like. In some embodiments, image scan data generated by an image scan system 116 may be stored in the scanned image data memory 118. This image scan data may include training examples, subject examples, tagged examples, actual subject scans, historical subject scans, and/or the like.

The communication devices 120 may correspond to at least one of a smart phone, tablet, personal computer, server, and/or some other computing device. Each communication device 120 may be configured with an operating system ("OS") and at least one communication application. The communication application may be configured to exchange communications between the communication device 120 and another component (e.g., a ADAQ system 104, elements dictionary memory 108, image scan system 116, scanned image data memory 118, another communication device 120, etc.) across the communication network 112. Additionally or alternatively, communications may be sent and/or received via the communication device 120 as a call, a packet or collection of packets (e.g., IP packets transmitted over an IP network), an email message, an instant message ("IM"), an SMS message, an MMS message, a video presentation, and/or combinations thereof.

Figure 2:
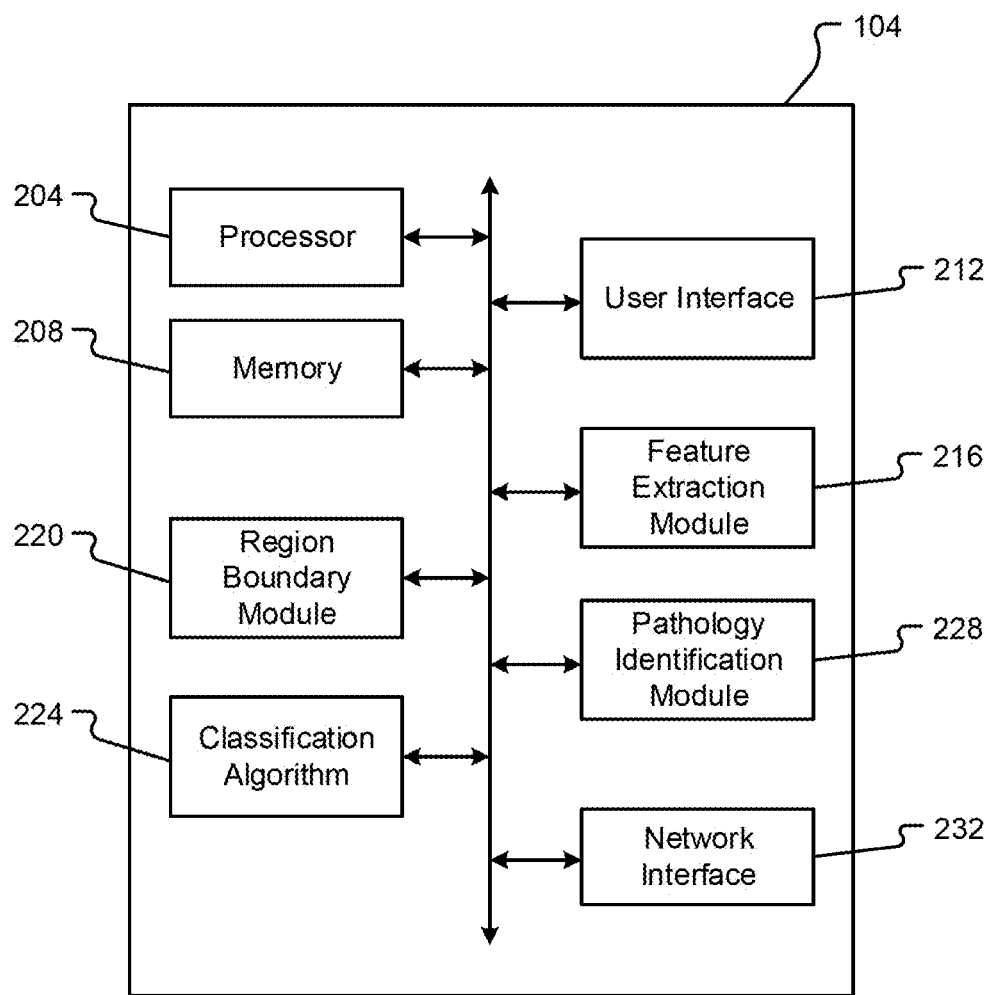
FIG. 2 is a block diagram depicting an automatic detection and quantification system in accordance with embodiments of the present disclosure.

Referring to FIG. 2, a block diagram depicting an ADAQ system 104 is shown in accordance with embodiments of the present disclosure. The ADAQ system 104 may include a processor 204 and a memory 208 that stores one or more instruction sets, applications, or modules, potentially in the form of a feature extraction module 216, a region boundary module 220, a pathology identification module 228, and/or a classification algorithm 224 (e.g., a support vector machine, etc.). The ADAQ system 104 may be configured as a server, or part of a server, that includes one or more of the components described in conjunction with FIG. 1. For instance, the ADAQ system 104 may include one or more elements dictionaries 108, scanned image data 118, and the like.

The processor 204 may correspond to one or more microprocessors that are contained within a common housing, circuit board, or blade with the memory 208. The processor 204 may be a multipurpose, programmable device that accepts digital data as input, processes the digital data according to instructions stored in its internal memory, and provides results as output. The processor 204 may implement sequential digital logic as it has internal memory. As with most microprocessors, the processor 204 may operate on numbers and symbols represented in the binary numeral system.

The memory 208 may correspond to any type of non-transitory computer-readable medium. In some embodiments, the memory 208 may comprise volatile or non-volatile memory and a controller for the same. Non-limiting examples of memory 208 that may be utilized in the ADAQ system 104 include RAM, ROM, buffer memory, flash memory, solid-state memory, or variants thereof. Any of these memory types may be considered non-transitory computer memory devices even though the data stored thereby can be changed one or more times.

The user interface 212 may be configured as a graphical user interface or other interface by which a user can interact with the ADAQ system 104. In some embodiments, results of an analysis performed by the ADAQ system 104 may be rendered by the user interface 212. The user interface 212 may be configured to display aspects of one or more of the components of the ADAQ system 104. Additionally or alternatively, the user interface 212 may be configured to present and/or render an application interface. The application interface may present a number of user interface elements to a user for one or more of training the system 104, defining or generating new element dictionaries 108, detecting and/or quantifying pathology from image data scans, and more. In one embodiment, the ADAQ system 104 may be configured in a client/server arrangement. For example, a communication device 120 may include a client application capable of interfacing with the ADAQ system 104 server. This arrangement may allow for shared processing, multiple users, a common server access, etc.

In some embodiments, the applications/instructions 216, 220, 224, 228 may correspond to any type of computer-readable instructions or files storable in the memory 208. The feature extraction module 216 may be configured to analyze an image data scan (e.g., a CT scan, etc.) of a subject and extract image blocks from within a defined area of the image data scan. In one embodiment, the feature extraction module 216 may utilize a fixed block size (e.g., 3.0 mm×3.0 mm) capture window moving within the defined area to extract image blocks. For instance, the capture window may be moved within a defined area along a path or vector. As the capture window moves from one position to another, the image falling inside the capture window at each defined position is saved to a memory, or extracted. This process continues until the capture window has moved along all programmed positions within the defined area.

The region boundary module 220 may be configured to automatically determine the defined area in an image data scan for feature extraction, etc. This defined area may be based on anatomical physiognomy, imaging fiducials, characteristic patterns, boundary definition information, etc., and/or combinations thereof. It is anticipated that the region boundary module 220 determines focused analysis areas for the ADAQ system 104. This approach eliminates the need for the ADAQ system 104 to perform an analysis of all areas of the image data scan. In some embodiments, the region boundary module 220 may determine sub-regions within a focus region to further analyze. Sub-regions may be defined for characteristic sections of an image or known patterns of types of pathology.

The classification algorithm 224 may be configured to generate the quantitative rules used in detecting pathology. The classification algorithm may include one or more of a support vector machine, logistic regression, random forest, nearest neighbors, etc. These machines and/or algorithms may be used separately or in combination as an ensemble to form the classification algorithm 224. In some cases, the ADAQ system 104 and/or the components of the ADAQ system 104 may include one more rules, conditions, predictive models, and/or methods generated by training the classification algorithm 224. For instance, the classification algorithm 224 may be presented a number of training examples. These training examples may include image data scans of healthy subjects, image data scans having pathology, and even image data scans identifying a particular pathology type. In some cases, the training of the classification algorithm 224 may include a diagnostic professional identifying regions of interest (e.g., those regions know to have pathology, etc.) of a number of image data scans. These regions of interest may be entered into the classifier algorithm 224 as a boundary within which the classification algorithm 224 (e.g., a support vector machine, etc.) will determine its pathology classifiers. In any event, the classification algorithm 224 may communicate with the elements dictionary memory 108 to determine the elements that can be used in providing a quantitative classification. In other words, the elements dictionary includes the language, or known elements/features, that can be used in differentiating between healthy and unhealthy tissue.

The pathology identification module 228 is configured to automatically determine whether pathology exists in one or more regions of an image data scan or scans. The pathology identification module 228 may utilize the elements in the element dictionary memory 108 to quantify regions of a received image data scan. Once quantified, the pathology identification module 228 may determine whether the quantitative value represents a specific pathology or pathology type. This determination may include viewing a plurality of regions and/or the quantitative value representing each region in the plurality of regions in a locality of the image data scan. The pathology identification module 228 may include quantitative rules for evaluating pathology, determining pathology type, identifying and/or marking areas, and even for generating results of the ADAQ system 104. In some embodiments, the pathology identification module 228 may communicate with the feature extraction module 216 in generating and/or updating the element dictionary 108

The network interface 232 may comprise hardware that facilitates communications with other elements, components, and/or devices over the communication network 112. The network interface 232 may include an Ethernet port, a Wi-Fi card, a Network Interface Card (NIC), a cellular interface (e.g., antenna, filters, and associated circuitry), or the like. The network interface 232 may be configured to facilitate a connection between the ADAQ system 104 and the communication network 112 and may further be configured to encode and decode communications (e.g., packets) according to a protocol utilized by the communication network 112.

Figure 3:
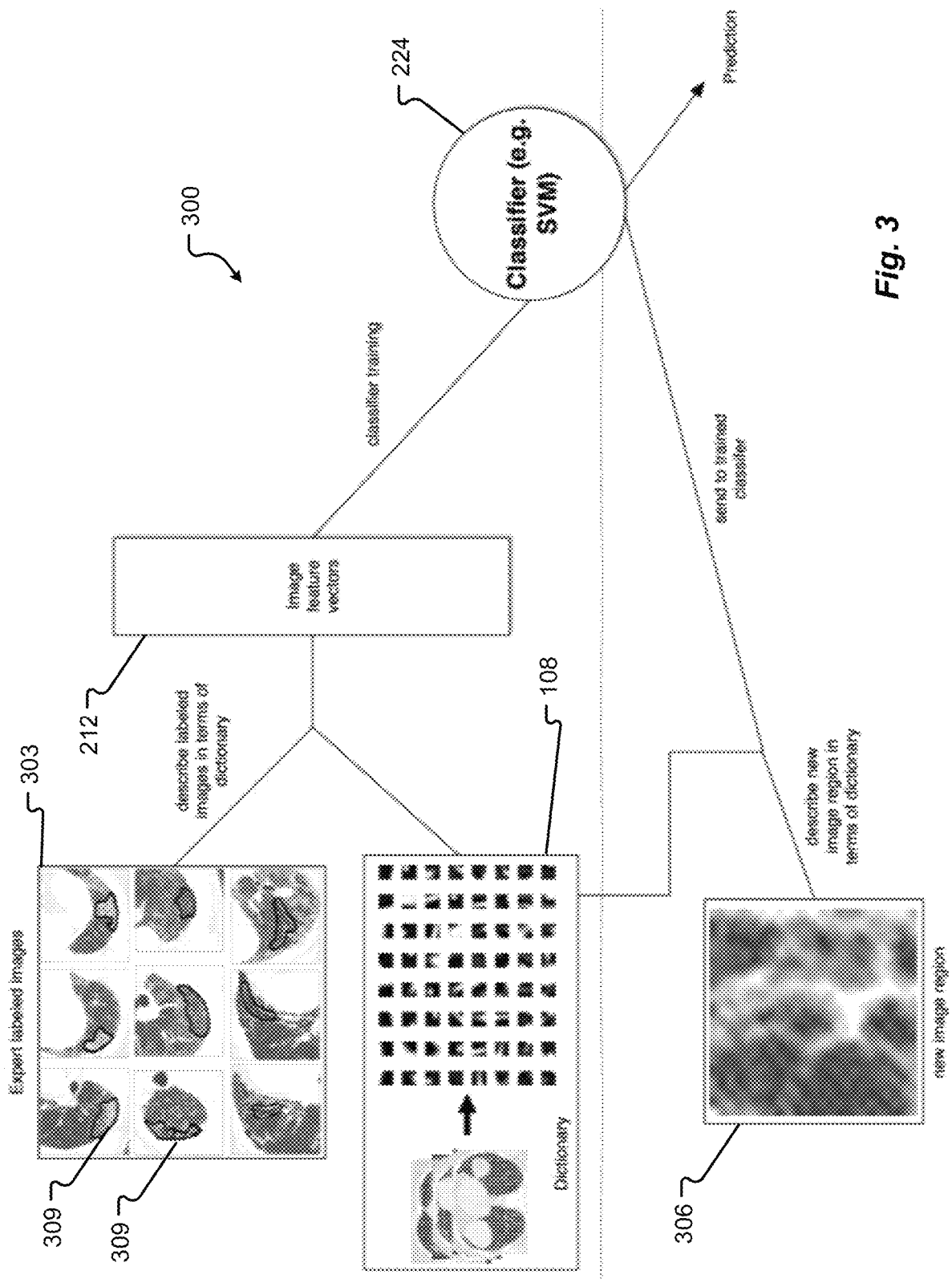
FIG. 3 is a block diagram depicting a method of training an automatic detection and quantification system and utilizing the trained automatic detection and quantification system in accordance with embodiments of the present disclosure.

FIG. 3 is a block diagram depicting a method 300 of training an automatic detection and quantification system and utilizing the trained automatic detection and quantification system in accordance with embodiments of the present disclosure. In training the machine learning algorithm (e.g., a support vector machine, etc.), a number of training images 303 may be presented to the ADAQ system 104. The training images 303 may be labeled (e.g., as healthy, unhealthy, by pathology and/or pathology type, etc.) and areas of concern (ROIs) may be marked 309. Among other things, the ADAQ system 104 may extract features 212 from these training images 303 to define quantitative pathology determination rules used in a predictive model. Upon receiving a new image 306, or an image data scan from a subject for diagnosis, the ADAQ system 104 automatically extracts the features as described herein and applies the predictive model to the extracted features or feature sets. An output of this application may be a label of whether a portion in the new image data scan includes healthy or unhealthy tissue regions. Areas of concern, or ROIs, in the new image region 306 may be automatically identified and marked via the ADAQ system 104. In one embodiment, an image of the marked areas of concern, or ROIs, may be visually identified by a highlight, mark, or other graphical report. This report may be rendered to the display of the ADAQ system 104 or at least one communication device 120.

Figure 4:
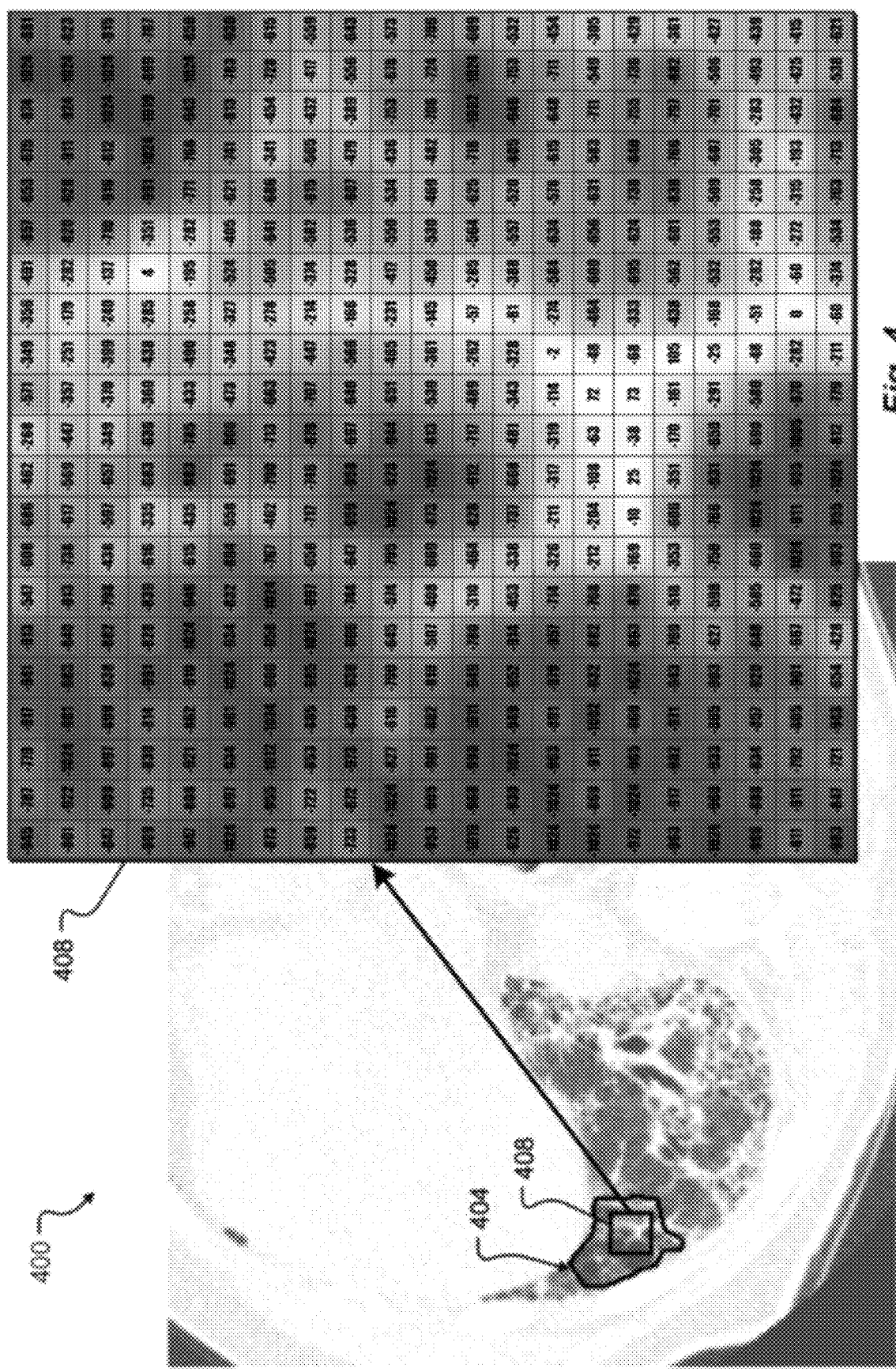
FIG. 4 shows a detail view of an image block of a subject image data scan in accordance with embodiments of the present disclosure.

FIG. 4 shows a detail view of an image block of a subject image data scan 400 in accordance with embodiments of the present disclosure. In particular, the subject image data scan 400 may include a region boundary 404 and a defined feature area 408 within the region boundary 404. As provided herein, the region boundary 404 may be determined automatically, or the region boundary 404 may be programmatically entered to focus or limit the feature extraction described herein. In any event, FIG. 4 shows the defined feature area 408 including approximately 441 pixels (e.g., in a 21-by-21 pixel feature area 408). Each pixel may have a specific pixel intensity or luminance value for its location that quantitatively describes a level of brightness or light intensity in a particular region. By way of example, the pixel in the first row, first column (1, 1) at the top left of the detail feature area 408 shows a luminance value of −945. Proceeding from left-to-right, the values read as follows: (1, 2)=−913; (1, 7)=−547; and so on. In some embodiments, the defined feature area 408 may define a specific pathology or type of a pathology. In one embodiment, a cluster of the pixels may define a specific pathology or type of a pathology. For instance, a capture window may be used to capture clusters of pixels that are adjacent to one another in the feature area 408. As provided herein, the capture window may include a fixed block size (e.g., in pixels or in physical dimension such as inches or millimeters, etc.) to determine relationships and characteristics of neighboring pixels. In determining a dictionary of elements to be used in the quantification of pathology, the information (e.g., luminance, histogram intensity, etc.) from each cluster of pixels obtained by the capture window as it moves throughout the defined feature area 408 are stored in a memory and grouped.

Figure 5:
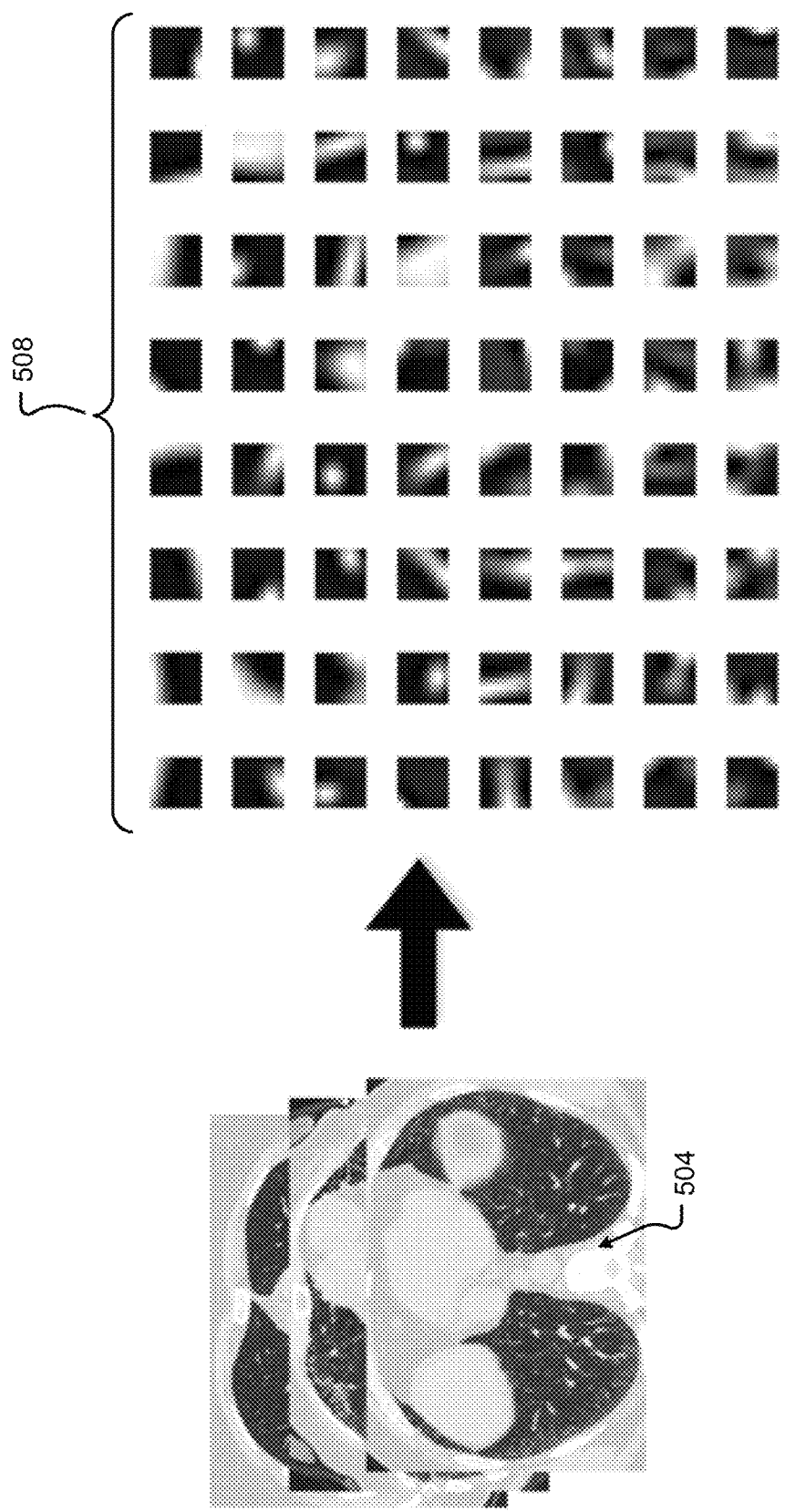
FIG. 5 is a diagram illustrating a set of dictionary elements generated from a number of image data scans in accordance with embodiments of the present disclosure.

FIG. 5 is a diagram illustrating a set of dictionary elements 508 generated from one or more image data scans 504 in accordance with embodiments of the present disclosure. The dictionary elements 508 shown in FIG. 5 include only 64 basis elements for the sake of clarity. It should be appreciated, however, that the set of dictionary elements may include any number of basis elements which can be used by the ADAQ system 104 in identifying, classifying, and quantifying pathology. In some embodiments, the overall approach described herein may be used in a hierarchical fashion to produce dictionaries of features at multiple scales. While embodiments disclosed herein describe classifying regions (which are described in terms of a dictionary of low-level features, etc.) using a trained SVM classifier, the present disclosure may include producing another dictionary at this scale instead —such that a second dictionary of features at a somewhat larger scale is generated and described in terms of the first dictionary at the smaller scale.

Figure 6:
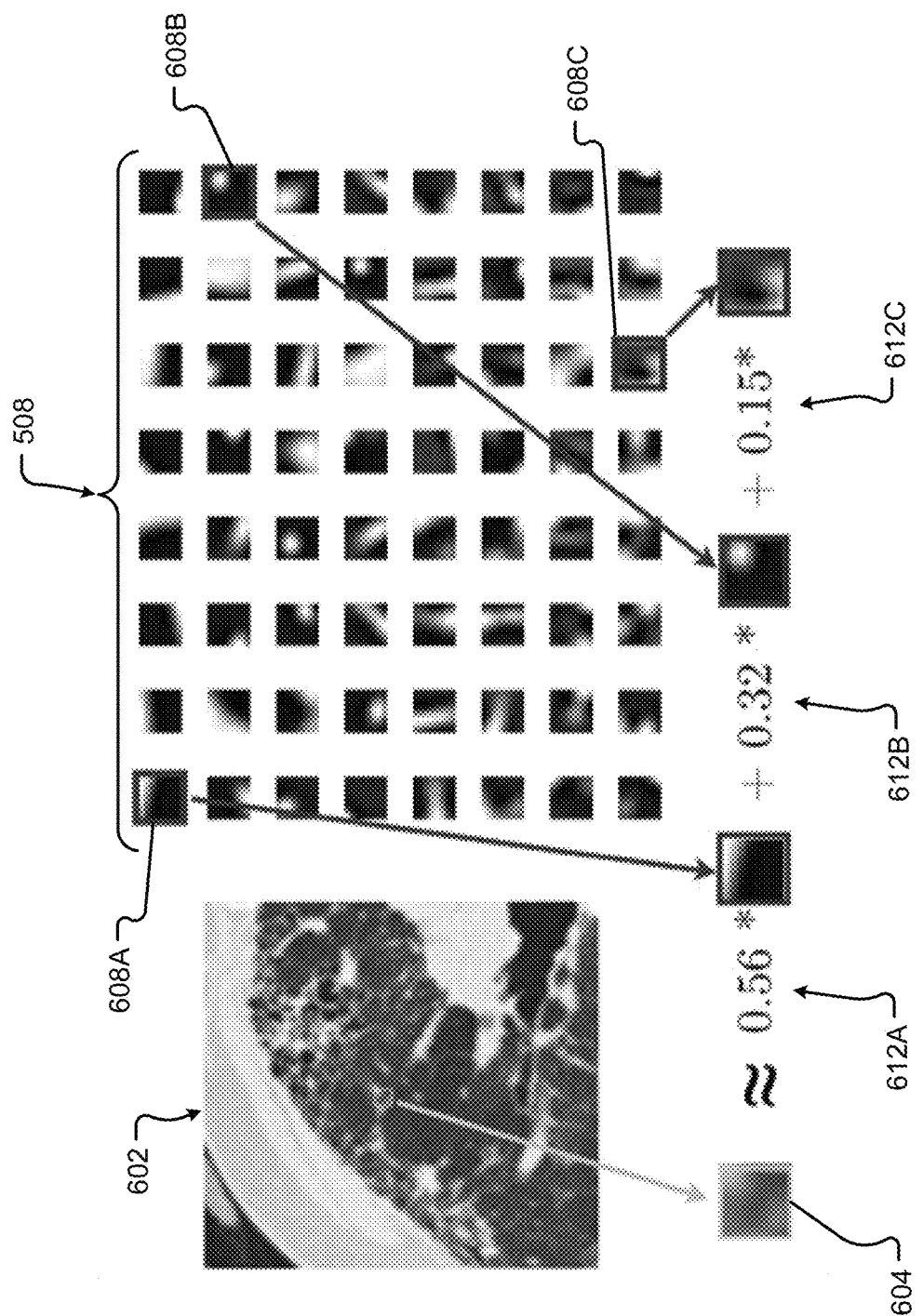
FIG. 6 is a diagram illustrating quantification of a subject region using the set of dictionary elements generated in accordance with embodiments of the present disclosure.

FIG. 6 is a diagram illustrating quantification of a subject region 604 using the set of dictionary elements 508 generated in accordance with embodiments of the present disclosure. Once the set of dictionary elements 508 is determined, a new image data scan 602 may be received by the ADAQ system 104. In FIG. 6, a subject region 604 is quantified based on, or using, the set of dictionary elements 508. The subject region 604 may be quantified using the light intensity, luminance, and/or histogram compared to the stored set of dictionary elements 508. By way of example, the subject region 604, or rather the regional/signature luminance of the subject region 604, is equivalent to 0.56 of basis element A 608A, plus 0.32 of basis element B 608B, plus 0.15 of basis element C 608C. As the subject region is not identical to any one of the basis elements in the set 508, each basis element used in calculating the signature for the subject region 604 luminance is adjusted by a scalar value 612A-C. This scalar adjustment allows for repeatable and accurate quantification of particular regions based on standardized dictionary elements for a pathology.

Figure 7:
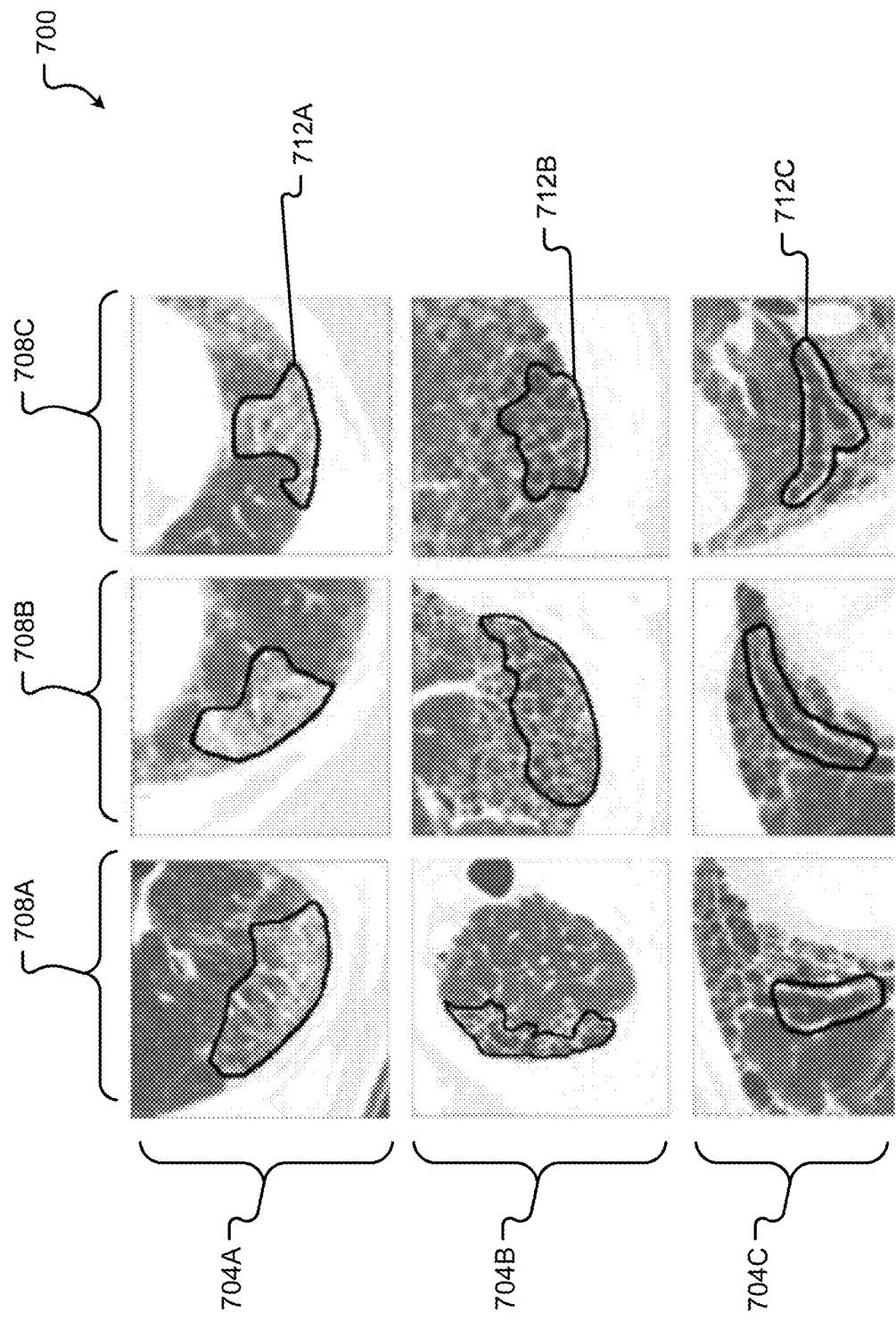
FIG. 7 shows a chart of image data scans grouped by identified pathology types in accordance with embodiments of the present disclosure.

FIG. 7 shows a chart 700 of image data scans grouped by identified pathology types in accordance with embodiments of the present disclosure. For instance, the first row 704A may include various image data scans associated with reticular abnormalities in IPF. The second row 704B may include image data scans of subject tissue associated with honeycombing in IPF. The third row 704C may include image data scans of subject tissue having traction bronchiectasis. As can be appreciated, each row may include one or more image data scans represented by the first, second, and third columns 708A-C. These image data scans may be used in training the ADAQ system 104 to predict pattern characteristics associated with various types of a pathology. In some cases, the characteristic patterns may be identified by an expert and delineated 712A, 712B, 712C for feature extraction and analysis by the ADAQ system 104.

Figure 8A:
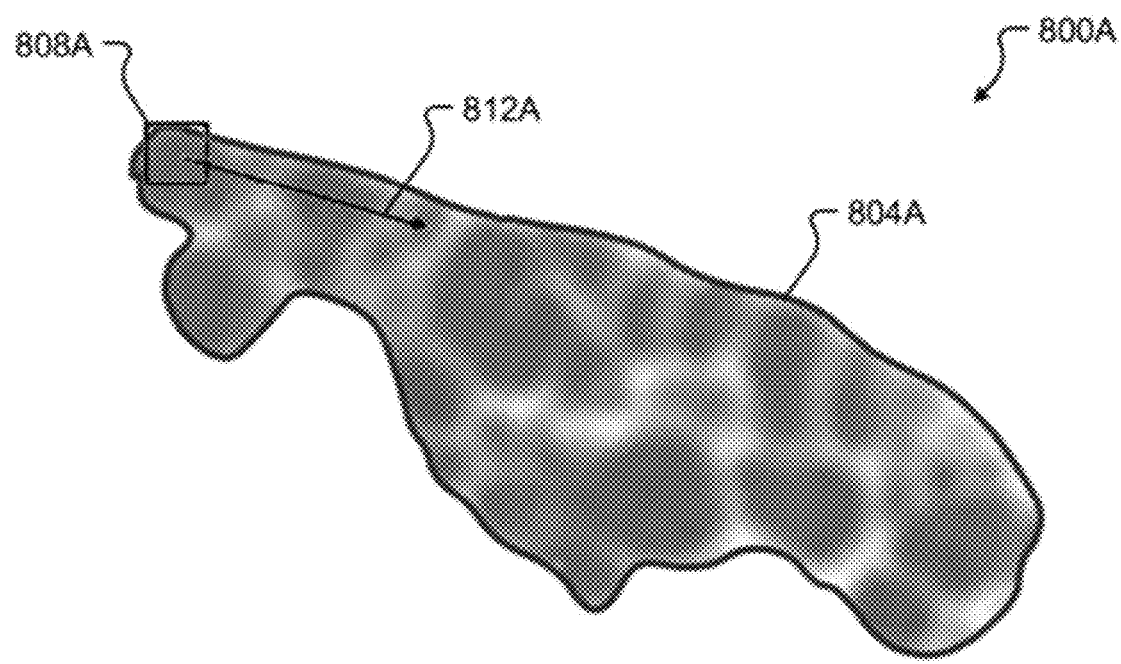
FIGS. 8A-8B show image blocks taken from image data scans used in vector quantization in accordance with embodiments of the present disclosure.
Figure 8B:
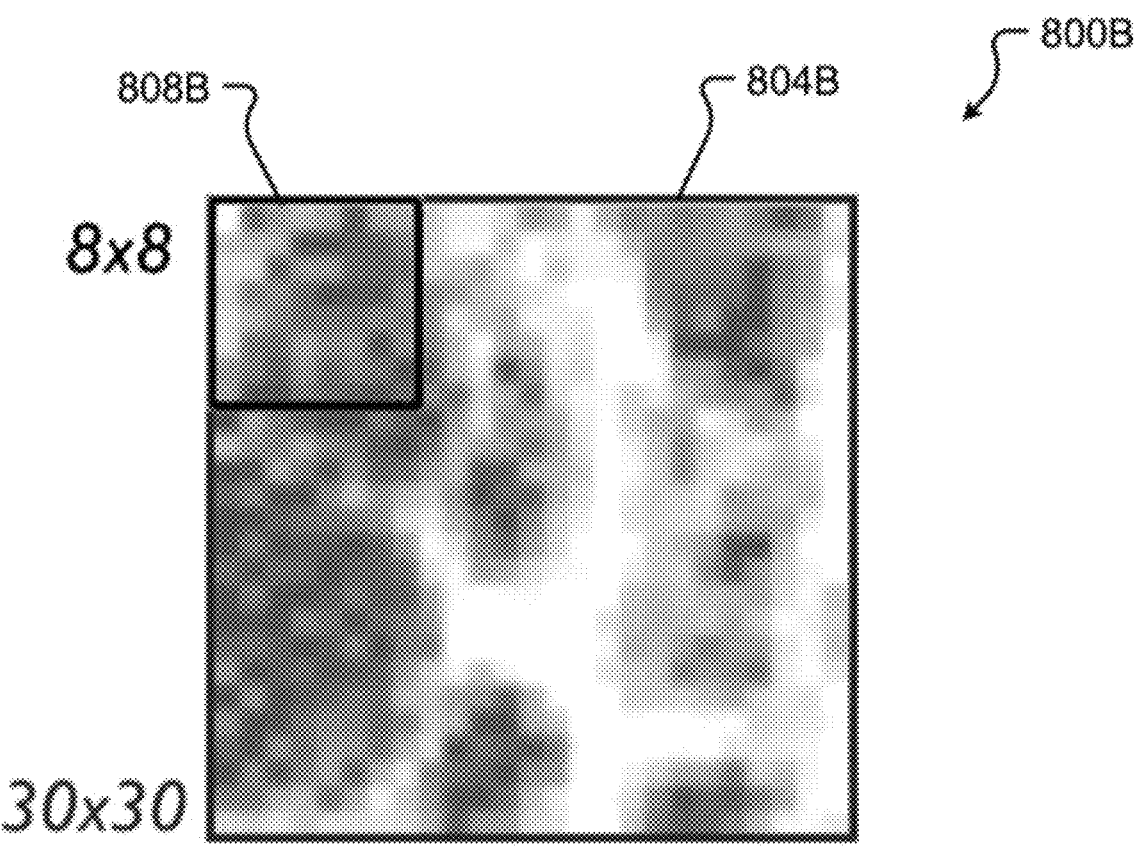

FIGS. 8A-8B show image blocks 800A-B taken from image data scans used in vector quantization in accordance with embodiments of the present disclosure. As shown in FIG. 8A a region of interest 804A may be delineated by an irregular-shaped boundary. As part of a feature extraction process, the capture window 808A may move within the region of interest 804A along a path defined by movement vector 812A, capturing and/or extracting features adjacent to one another (e.g., adjacent fixed size capture windows, overlapping windows, etc.). Depending on the context, the features captured in this process may be used in training the ADAQ system 104 or in identifying and quantifying pathology in an image data scan. FIGS. 8A-8B may correspond to "pooling," where the dictionary may contain "low-level" features (e.g., in the 8×8 square capture window 808A, 808B) and regions to be classified are larger (804A, 804B). Average, maximum, and/or other methods for pooling, weighting coefficients for all overlapping capture blocks 808A, 808B within the regions 804A, 804B can produce a feature vector for their respective region 804A, 804B that is then the input to the SVM or other classifier (e.g., classification algorithm 224, etc.).

FIG. 8B includes a region of interest 804B delineated by a square boundary. In some embodiments, a region of interest 804B may comprise a 30 by 30 pixel square. Similar to FIG. 8A, as part of a feature extraction process, the capture window 808B may move within the region of interest 804B along one or more axes, capturing and/or extracting features in adjacent to one another (e.g., adjacent fixed size capture windows, overlapping windows, etc.). In some embodiments, the capture window 808B may comprise a square of 8 by 8 pixels. Depending on the context, the features captured in this process may be used in training the ADAQ system 104 or identifying and quantifying pathology in an image data scan. In some embodiments, the square region may be taken from within the irregular-shaped boundary described in FIG. 8A. Sampling irregularly shaped regions (as shown in FIG. 8A) in new images may be performed with an image processing method called "superpixels." Using this method may allow for an efficient sampling of new images. For example, simply sampling or extracting square regions may result in incomplete or mixed patterns within the region since natural images tend not to follow regular square shaped blocks.

Figure 9B:
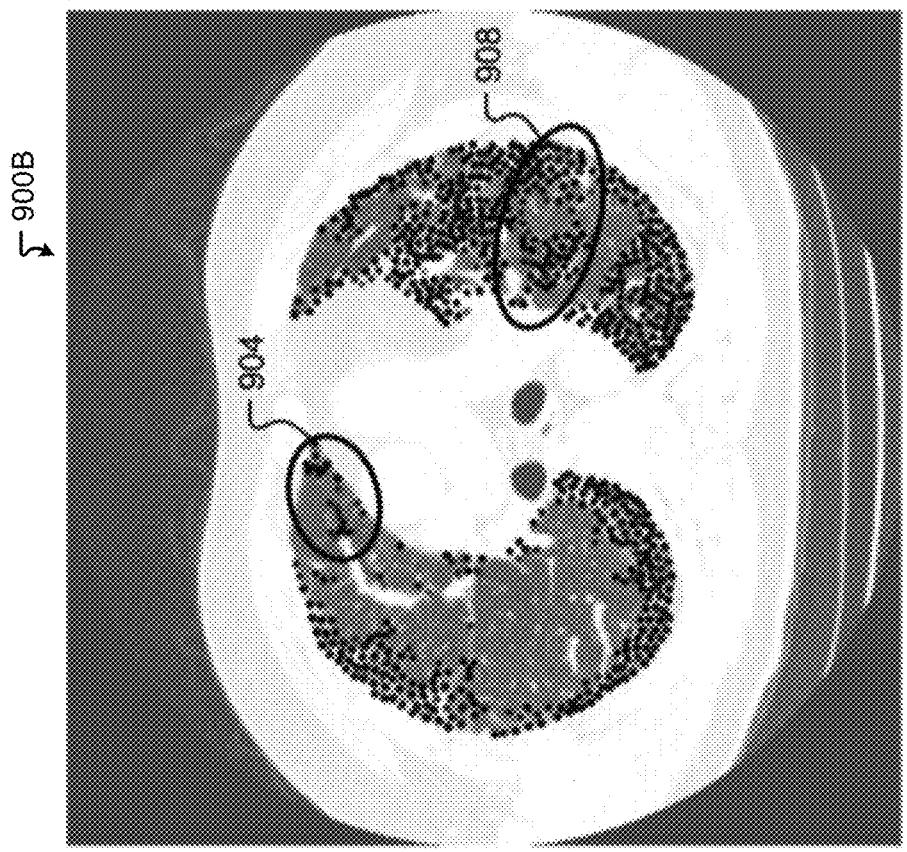
FIG. 9B is a diagram of an image data scan including identified regions of interest by the automatic detection and quantification system in accordance with embodiments of the present disclosure.
Figure 9A:
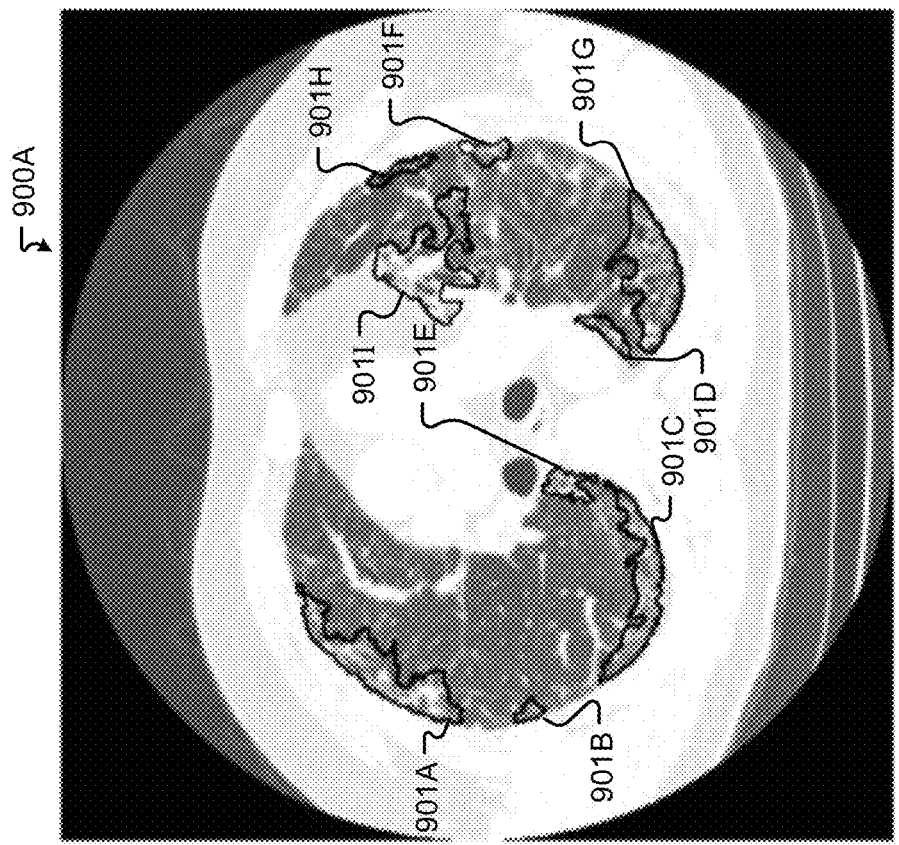
FIG. 9A is a diagram of an image data scan including human identified regions of interest.

FIG. 9A is a diagram of an image data scan 900A including human identified regions of interest. As shown in the image data scan 900A of FIG. 9A, an expert or diagnostic professional may determine one or more regions of interest 901A-I by outlining or otherwise marking areas in the scan. However, as there are many image data scans and interpretation bias between experts (e.g., inter-observer variations, etc.) the expert may not accurately determine all pathology or relevant regions of interest.

FIG. 9B is a diagram of an image data scan 900B including identified regions of interest by the ADAQ system 104 in accordance with embodiments of the present disclosure. The quantitative analysis performed by the ADAQ system 104 removes any variation or bias and may determine regions of interest that escape the attention of an expert. For example, FIG. 9B includes a first area 904 and a second area 908 that went unidentified by a human expert (e.g., described and shown in conjunction with FIG. 9A).

FIG. 10A shows a sample image data scan 1000A of a subject in accordance with embodiments of the present disclosure. As provided above, the image data scan 1000A may be a CT scan of a section of a subject lungs. In the sample image data scan 1000A of FIG. 10A no pathology may be visually detected by an expert. However, pathology may be evident to the ADAQ system 104, which can detect characteristic patterns based on the dictionary of elements generated for a pathology. Because the ADAQ system 104 uses feature extraction for elements on a pixel cluster bases, the ADAQ system 104 can detect pathology that is undetectable by the human eye. For example, FIG. 10B shows the image data scan of FIG. 10A including at least three human-undetectable regions of interest 1004, 1008, 1012 that can be detected and identified by the ADAQ system 104 in accordance with embodiments of the present disclosure.

Figure 11:
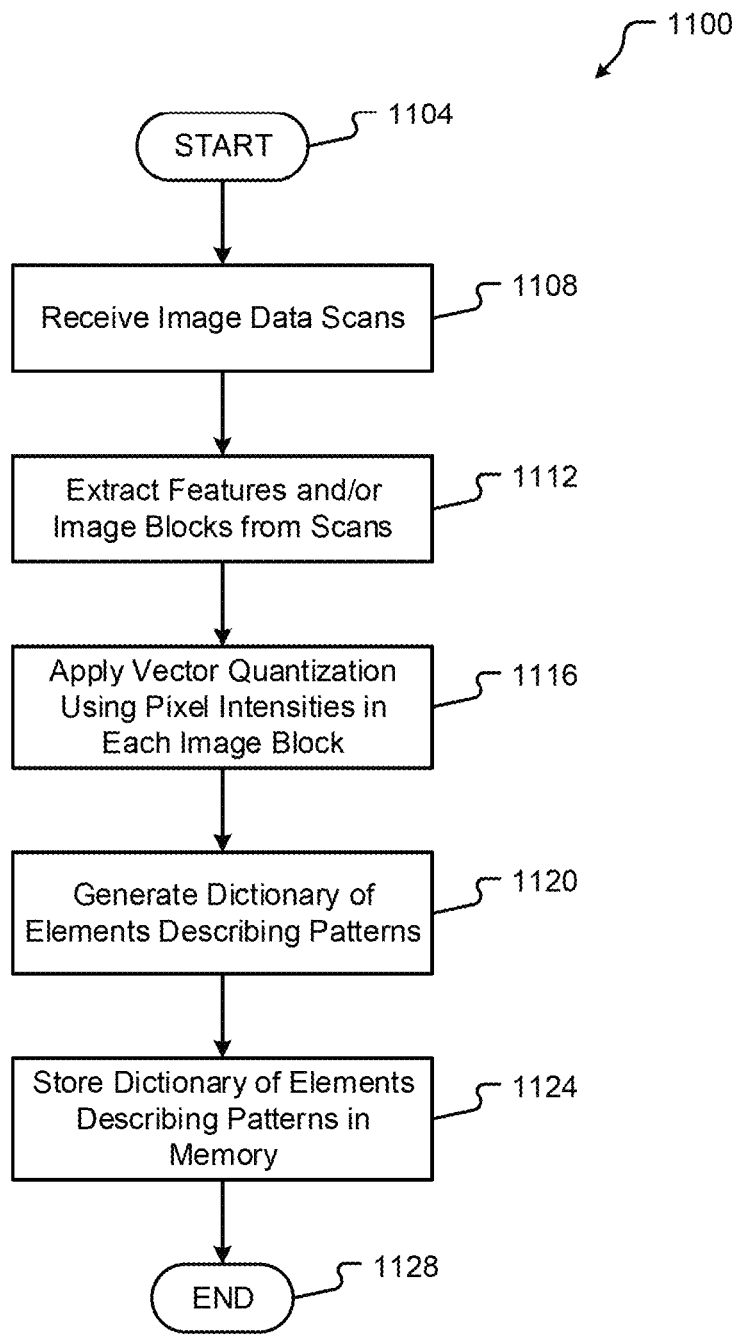
FIG. 11 is a flow chart depicting a method of generating a dictionary of elements in accordance with embodiments of the present disclosure.

FIG. 11 is a flow chart depicting a method 1100 of generating a dictionary of elements in accordance with embodiments of the present disclosure. While a general order for the steps of the method 1100 is shown in FIG. 11, the method 1100 can include more or fewer steps or can arrange the order of the steps differently than those shown in FIG. 11. Generally, the method 1100 starts with a start operation 1104 and ends with an end operation 1128. The method 1100 can be executed as a set of computer-executable instructions executed by a computer system and encoded or stored on a computer readable medium. Hereinafter, the method 1100 shall be explained with reference to the systems, components, modules, software, data structures, user interfaces, etc. described in conjunction with FIGS. 1-10.

The method 1100 begins at 1104 and proceeds by receiving image data scans (step 1108). These image data scans may be received by the ADAQ system 104. As provided above, the image data scans may be generated by one or more image scan systems 116 and may even be associated with a number of different subjects. In some embodiments, the image data scans represent a digital image of a cross-section of at least one area or volume of a subject (e.g., a patient, animal, etc.). The image data scans may be sent by the image scan system 116 across a communication network 112 with which the ADAQ system 104 is communicatively connected. In some embodiments, the ADAQ system 104 may retrieve the images from a database, a scanned image data memory 118, an image scan system 116, and/or some other memory.

The method 1100 continues by extracting features and/or image blocks from each of the image data scans (step 1112). In some embodiments, the feature extraction may include defining a fixed block size for data collection. In other words, the fixed block size may define the size (e.g., area, length, width, dimension etc.) of each basis element in the dictionary of elements. Images may be volumetric (3D) and/or contain multi-modal information (i.e., combinations of various imaging modalities to create a composite image). The fixed block size may correspond to a capture window size that is used to collect information from the image data scan or a region thereof. For example, as the capture window moves along a path and/or within a delineated area of the image data scan, the capture window can store features as image blocks in one or more memories associated with the ADAQ system 104. In some embodiments, a pre-processing step may include standardizing blocks (e.g., so mean pixel value is zero and standard deviation is 1.0, etc.). Additionally or alternatively, data "whitening" or other type of mathematical filtering may be used.

Next, the method 1100 proceeds by applying vector quantization using pixel intensities in each image block captured/extracted (step 1116). In this step, the ADAQ system 104 may divide the collection of different pixel clusters having specific intensities and locations into specific groups defining recurring patterns. These patterns may serve to indicate various states of tissue in an image scan including, but in no way limited to, healthy, unhealthy, deteriorating, and/or variations thereof.

Using the grouped information, the method 1100 continues by generating a dictionary of elements describing the patterns of extracted features (step 1120). Generating the dictionary may include a set of basis elements that represent the patterns determined through vector quantization, etc. The basis elements may later be used to quantify pathology and/or tissue in image data scans. It is anticipated that a dictionary of elements may be generated for specific regions of a subject, specific pathologies, specific types of a particular pathology, etc., and/or combinations thereof. In some cases, the dictionary of elements may be further refined by repeating the method 1100 using additionally received image data scans. In some embodiments, dictionaries may also be refined using other methods, possibly feature selection methods to optimize number of elements in a dictionary or other methods to update dictionary elements to maximize classification accuracy. Additionally or alternatively, the methods, devices, and systems described herein may be employed to generate multiple dictionaries at different scales—"layers" of dictionaries describing hierarchical features, etc. The dictionary of elements may include a fixed number of basis elements for specific quantization of pathology.

Once generated, the dictionary of elements may be stored in a memory (step 1124). This memory may be associated with the ADAQ system 104 and may be stored remotely from and/or locally with the ADAQ system. In one embodiment, the dictionary of elements may be stored in the cloud accessible via a communication network 112. In any event, the method 1100 ends at step 1128.

Figure 12:
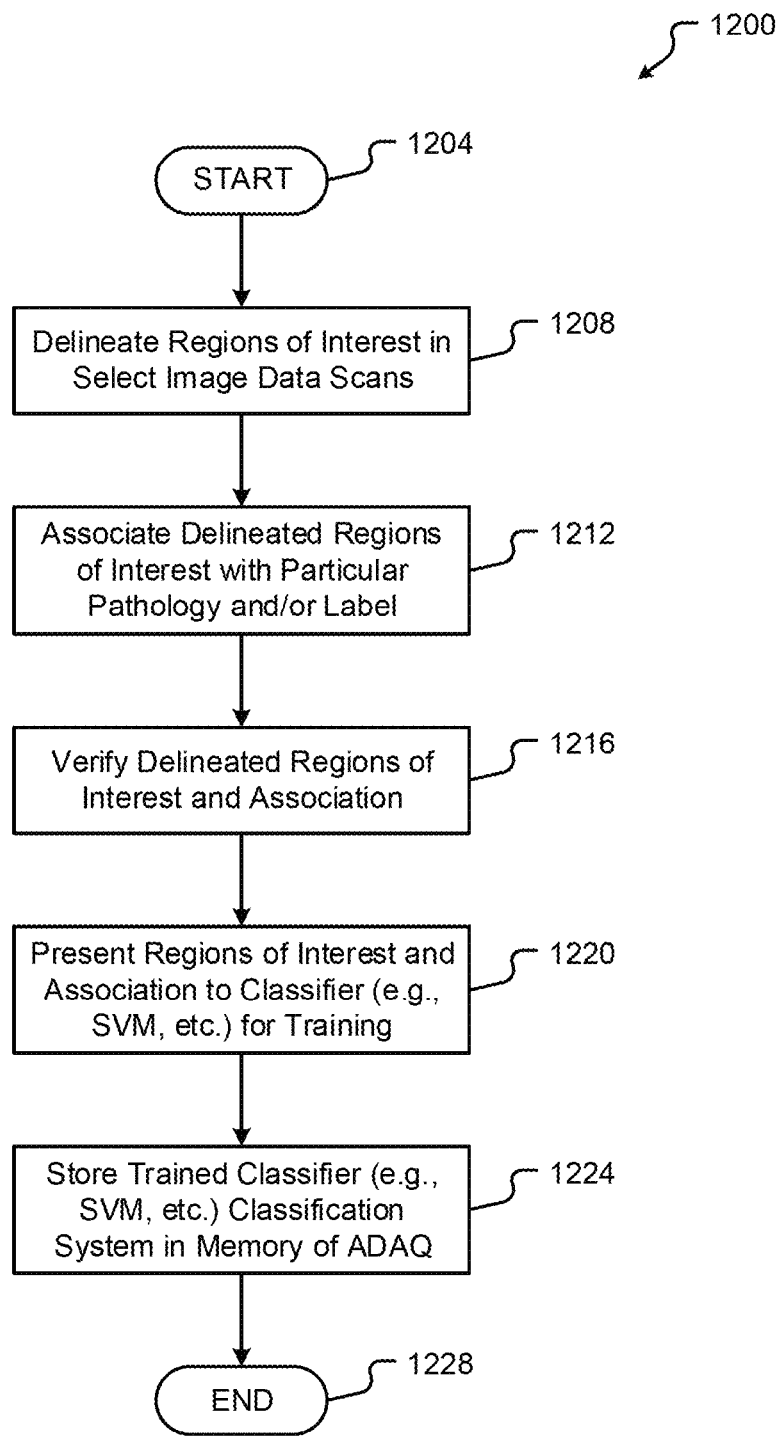
FIG. 12 is a flow chart depicting a method of training an automatic detection and quantification system in accordance with embodiments of the present disclosure.

FIG. 12 is a flow chart depicting a method 1200 of training an ADAQ system 104 in accordance with embodiments of the present disclosure. While a general order for the steps of the method 1200 is shown in FIG. 12, the method 1200 can include more or fewer steps or can arrange the order of the steps differently than those shown in FIG. 12. Generally, the method 1200 starts with a start operation 1204 and ends with an end operation 1228. The method 1200 can be executed as a set of computer-executable instructions executed by a computer system and encoded or stored on a computer readable medium. Hereinafter, the method 1200 shall be explained with reference to the systems, components, modules, software, data structures, user interfaces, etc. described in conjunction with FIGS. 1-11.

The method 1200 begins at step 1204 and proceeds by delineating regions of interest in select image data scans (step 1208). In some embodiments, the select image data scans may be taken from the image data scans used in generating the dictionary of elements described in conjunction with FIG. 11. The delineation may be performed by a diagnostic professional or an expert. In some cases, the delineation is used to define regions of interest in the image data scans having pathology or a specific type of a pathology. Delineation may include the expert outlining these regions of interest using a digitizing pen and surface (e.g., tablet, screen, etc.). By way of example, an image data scan having pathology may be displayed to a user interface display device. The expert may determine the image includes a region of pathology. Then, the expert may use the digitizing pen to outline, or highlight, the region of interest. The delineated image or region may then be saved to memory.

Next, the delineated image may be associated with a particular pathology and/or a label (step 1212). For instance, the expert may have identified the pathology delineated as IPF in the image data scan. Additionally or alternatively, the expert may determine that the delineated region includes a particular manifestation, or type, of IPF such as honeycombing. In any event, the delineated image may be saved with a label, grouped, or otherwise identified with the particular pathology and/or type of particular pathology. In some embodiments, this label may be read by the ADAQ system 104 upon reviewing the delineated region, related basis elements in the dictionary of elements, and/or the delineated image data scan. The delineated regions and their labels may be stored in memory serving to capture the expert work product.

In some cases, the method 1200 may continue by verifying the delineated regions of interest and any associated labels/identifications (step 1216). This verification may be performed by a second different expert and/or diagnostic professional. The verification may include a blind study of the image data scans where the second expert is required to delineate regions of interest in unmarked image data scans. In one embodiment, the verification may include the second expert reviewing the marked or delineated image data scans for accuracy. Any differences are noted and saved with the delineated image data scans.

Next, the delineated regions of interest and accompanying association labels are presented to the ADAQ system 104 (e.g., the classification algorithm 224, etc.) for training (1220). In training the ADAQ system 104, the dictionary of elements, healthy image data scans, unhealthy image data scans (e.g., the delineated image data scans having pathology, etc.) are provided to the support vector machine or other classification algorithm 224 (e.g., as training examples) to determine a classification model for use in quantifying pathology in any image data scan. The classification model is capable of performing an analysis of an image data scan and determine a quantified value representing whether and to what extent the image data scan includes pathology markers.

The method 1200 continues by storing the trained classification system, or classification model, in a memory associated with the ADAQ system 104 (step 1224). This memory may be associated with the ADAQ system 104 and may be stored remotely from and/or locally with the ADAQ system 104. In one embodiment, the classification model may be stored in the cloud and be accessible across a communication network 112. In any event, the method 1200 ends at step 1228.

Figure 13:
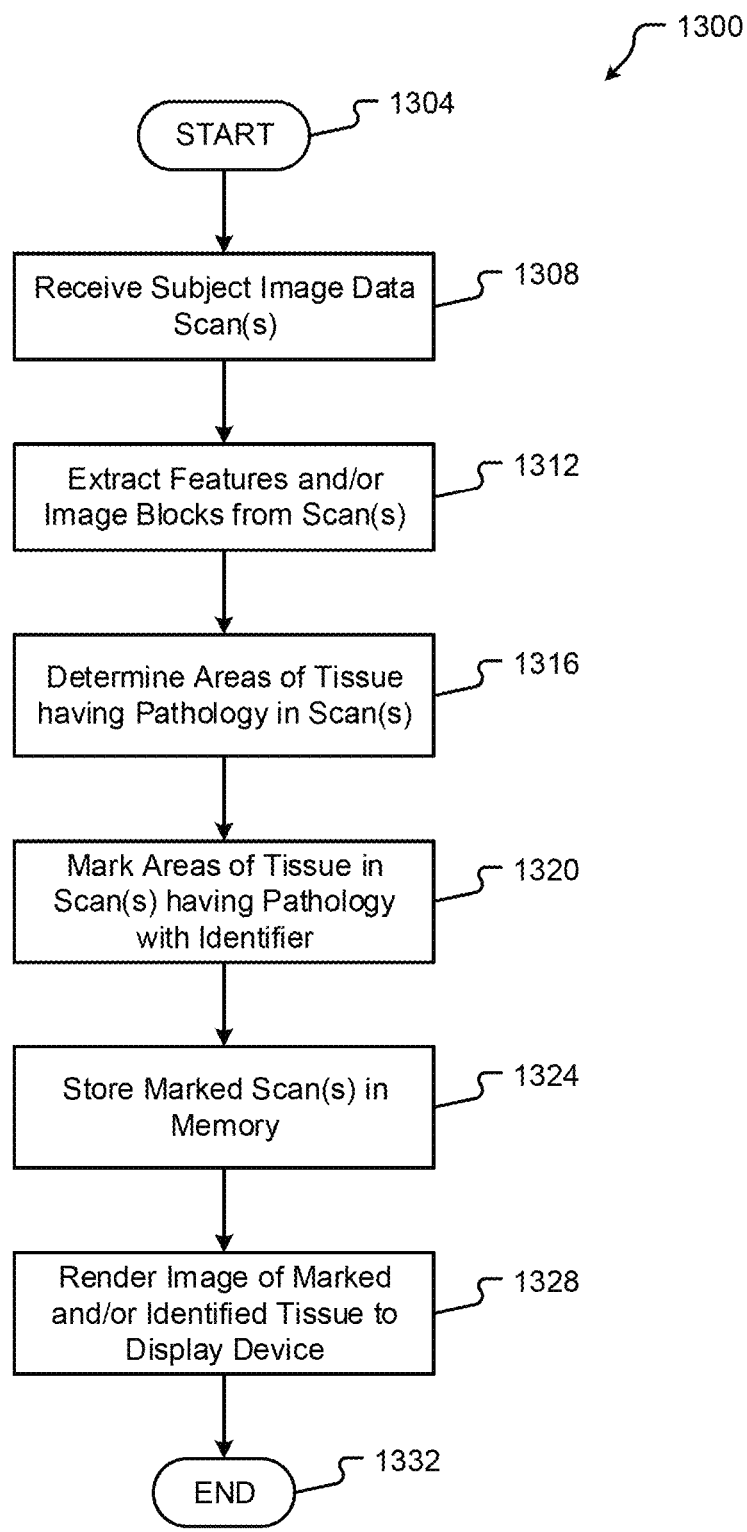
FIG. 13 is a flow chart depicting a method of identifying pathology in the automatic detection and quantification of pathology in accordance with embodiments of the present disclosure.

FIG. 13 is a flow chart depicting a method 1300 of identifying pathology in the automatic detection and quantification of pathology in accordance with embodiments of the present disclosure. While a general order for the steps of the method 1300 is shown in FIG. 13, the method 1300 can include more or fewer steps or can arrange the order of the steps differently than those shown in FIG. 13. Generally, the method 1300 starts with a start operation 1304 and ends with an end operation 1332. The method 1300 can be executed as a set of computer-executable instructions executed by a computer system and encoded or stored on a computer readable medium. Hereinafter, the method 1300 shall be explained with reference to the systems, components, modules, software, data structures, user interfaces, etc. described in conjunction with FIGS. 1-12.

The automatic detection and quantification of pathology method 1300 begins at step 1304 and proceeds by receiving image data scans for a subject (step 1308). In some embodiments, these image data scans may be associated with a single subject, or individual, to determine whether any pathology in the scans exist. The image data scans may be generated by one or more image scan systems 116. As provided above, the image data scans represent a digital image of a cross-section of at least one area or volume of a subject (e.g., a patient, animal, etc.). The image data scans may be sent by the image scan system 116 across a communication network 112 with which the ADAQ system 104 is communicatively connected. In some embodiments, the ADAQ system 104 may retrieve the images from a database, a scanned image data memory 118, an image scan system 116, and/or some other memory.

Next, the method 1300 continues by extracting features and/or image blocks from each of the image data scans (step 1312). In some embodiments, the feature extraction may include defining a fixed block size for data collection. In other words, the fixed block size may define the size (e.g., area, length, width, etc.) that corresponds to the size used in generating each of the basis elements in the dictionary of elements. Similarly, the fixed block size may correspond to a capture window size that is used to collect information from the image data scan or a region thereof. For example, as the capture window moves along a path and/or within the image data scan, the capture window can store features as image blocks in one or more memories associated with the ADAQ system 104.

The method 1300 proceeds by determining whether any areas of tissue illustrated in the image data scans received include pathology (step 1316). In some embodiments, the ADAQ system 104 may apply the classification model described in conjunction with FIG. 12, to the collected information and extracted feature blocks from the image data scans received in step 1308 (step 1316). The determination may include classifying each feature block as a quantified value using the set of basis elements in the element dictionary. This classification is described in greater detail in conjunction with FIGS. 5 and 6. For example, each feature block may be valued as at least one basis element multiplied by a scalar value. Similar to the values determined for the dictionary of elements, the extracted feature blocks are classified by pixel intensity and feature similarity to basis elements in the dictionary.

Any tissue determined to have pathology, via the automatic determination described in step 1316, is marked with an identifier (step 1320). Each identifier may be associated with a row and column position in a particular image data scan. In some cases, the identifier may define a region or boundary around a group of pixels in an image data scan. The region may be defined by a measurement value associated with the scan. In some embodiments, the region or boundary may be defined by pixel position in the image data scan. In any event, the identifier is associated with a particular image data scan.

Next, the method 1300 stores the image data scan including the identification marking (step 1324). This may include storing a new version or file of the image data scan that includes markings of pathology. The marked image data scans may be stored in any memory described herein.

In some embodiments, the method 1300 may proceed by rendering the identifier of pathology to a display device (step 1328). As provided above, the identifier may provided on a modified image data scan. For instance, the identifier may highlight the location of any detected pathology. In some embodiments, the identifier may classify the pathology type. As can be appreciated, this marking may be rendered to the display of a communication device 120, the ADAQ system 104, the image scan system 116, or any other device communicatively coupled to the ADAQ system 104. The marking may utilize one or more color, shape, size, hatching, area fill, shading, line type, line thickness, and/or other visual application to illustrate the pathology location and/or type. In some embodiments, a report may be generated for the results determined. For example, the report may be include a score, which in the IPF example may be fibrosis score based on fraction of regions tested that are classified as fibrosis (e.g., score=(#regions class. fibrotic)/(total #regions tested), etc.).

In some cases, the identification of pathology may be accompanied by a report. The report may provide a quantification of the amount of pathology in a subject, in a region, and/or in a scan. Moreover, the report may summarize an overall stage of the pathology. In any event, the report may be rendered to the display device. It is an aspect of the present disclosure that an alarm is provided when pathology is detected above a threshold value. In some cases, the alarm may indicate that treatment of the pathology, if available or possible, is associated with a particular level of urgency. The alarm and/or any levels, descriptions, or accompanying information may be rendered via the display device. The method 1300 ends at step 1332.

The exemplary systems and methods of this disclosure have been described in relation to computers, imaging devices, diagnostic devices, systems, and methods in a pathology detection system. However, to avoid unnecessarily obscuring the present disclosure, the preceding description omits a number of known structures and devices. This omission is not to be construed as a limitation of the scopes of the claims. Specific details are set forth to provide an understanding of the present disclosure. It should, however, be appreciated that the present disclosure may be practiced in a variety of ways beyond the specific detail set forth herein. Moreover, it should be appreciated that the methods disclosed herein may be executed via a wearable device, a mobile device, a reading device, a communication device, and/or an access server of an access control system, etc.

Furthermore, while the exemplary aspects, embodiments, options, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, such as a Personal Computer (PC), laptop, netbook, smart phone, Personal Digital Assistant (PDA), tablet, etc., or collocated on a particular node of a distributed network, such as an analog and/or digital telecommunications network, a packet-switch network, or a circuit-switched network. It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or more communications devices, at one or more users' premises, or some combination thereof. Similarly, one or more functional portions of the system could be distributed between a telecommunications device(s) and an associated computing device.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

Optionally, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

Any of the steps, functions, and operations discussed herein can be performed continuously and automatically.

Examples of the processors as described herein may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture. In some embodiments, functions may be performed by one or more graphics processing units (GPUs). Such GPUs may include, but are not limited to, at least one of an Nvidia Titan Xp or similar (GTX 1080 Ti, GTX 1070, GTX 1080, etc.).

What is claimed is:

1. An automatic detection and quantification system comprising:
   a processor; and
   a computer readable medium, coupled to the processor and comprising instructions stored thereon that cause the processor to:
      receive an input image data scan of a subject;
      extract features from the input image data scan;
      determine, using an elements dictionary and a classification model, one or more normal and/or abnormal pathology areas of the input image data scan based on the extracted features, wherein each pathology area comprises a cluster of pixels;
      compute one or more quantitative scores for the input image data scan based on a comparison of a number of regions classified as various categories of normal and/or abnormal with a number of regions tested; and
      render an image comprising the input image data scan with each of the determined one or more pathology areas marked with a visual identifier and the computed one or more quantitative scores for the input image.

2. The automatic detection and quantification system of claim 1, wherein the instructions further cause the processor to generate the elements dictionary based on a plurality of sample image data scans received from a plurality of subjects.

3. The automatic detection and quantification system of claim 2, wherein the plurality of sample image data scans comprises healthy image data scans and pathology image data scans.

4. The automatic detection and quantification system of claim 2, wherein the instructions further cause the processor to generate multiple elements dictionaries based on sample image data scans received from different subjects of the plurality of subjects.

5. The automatic detection and quantification system of claim 2, wherein the instructions further cause the processor to determine a set of basis elements for the dictionary of elements, wherein each element of the set of basis elements represents a group of similar features.

6. The automatic detection and quantification system of claim 1, wherein the instructions further cause the processor to calculate two or more quantitative scores based on the comparison of the number of regions classified as various categories of normal and/or abnormal with the number of regions tested.

7. The automatic detection and quantification system of claim 6, wherein the image is rendered by marking each of the determined one or more normal and/or abnormal pathology areas on the input image data scan with the visual identifier.

8. A method comprising:
   receiving, with a processor, an input image data scan of a subject;
   extracting, with the processor, features from the input image data scan;
   determining, with the processor, using an elements dictionary and a classification model, one or more normal and/or abnormal pathology areas of the input image data scan based on the extracted features, wherein each pathology area comprises a cluster of pixels;
   computing, with the processor, one or more quantitative scores for the input image data scan based on a comparison of a number of regions classified as various categories of normal and/or abnormal with a number of regions tested; and rendering an image comprising the input image data scan with each of the determined one or more pathology areas marked with a visual identifier and the computed one or more quantitative scores for the input image.

9. The method of claim 8, further comprising generating, with the processor, the elements dictionary based on a plurality of sample image data scans received from a plurality of subjects.

10. The method of claim 9, wherein the plurality of sample image data scans comprises healthy image data scans and pathology image data scans.

11. The method of claim 9, further comprising generating multiple elements dictionaries based on sample image data scans received from different subjects of the plurality of subjects.

12. The method of claim 9, further comprising determining a set of basis elements for the dictionary of elements, wherein each element of the set of basis elements represents a group of similar features.

13. The method of claim 9, further comprising calculating two or more quantitative scores based on the comparison of the number of regions classified as various categories of normal and/or abnormal with the number of regions tested.

14. The method of claim 8, wherein the image is rendered by marking each of the determined one or more normal and/or abnormal pathology areas on the input image data scan with the visual identifier.

15. A computer system comprising:
a processor; and
a computer readable medium, coupled to the processor and comprising instructions stored thereon that cause the processor to:
receive an input image data scan of a subject;
extract features from the input image data scan;
determine, using an elements dictionary and a classification model, one or more normal and/or abnormal pathology areas of the input image data scan based on the extracted features, wherein each pathology area comprises a cluster of pixels;
compute one or more quantitative scores for the input image data scan based on a comparison of a number of regions classified as various categories of normal and/or abnormal with a number of regions tested; and
render an image comprising the input image data scan with each of the determined one or more pathology areas marked with a visual identifier and the computed one or more quantitative scores for the input image.

16. The computer system of claim 15, wherein the instructions further cause the processor to generate the elements dictionary based on a plurality of sample image data scans received from a plurality of subjects.

17. The computer system of claim 16, wherein the plurality of sample image data scans comprises healthy image data scans and pathology image data scans.

18. The computer system of claim 16, wherein the instructions further cause the processor to generate multiple elements dictionaries based on sample image data scans received from different subjects of the plurality of subjects.

19. The computer system of claim 16, wherein the instructions further cause the processor to determine a set of basis elements for the dictionary of elements, wherein each element of the set of basis elements represents a group of similar features.

20. The computer system of claim 15, wherein the instructions further cause the processor to calculate two or more quantitative scores based on the comparison of the number of regions classified as various categories of normal and/or abnormal with the number of regions tested.

* * * * *